(12) United States Patent
Bencsits

(10) Patent No.: US 8,642,663 B2
(45) Date of Patent: Feb. 4, 2014

(54) ACETALS AS INSECT REPELLANT AGENTS

(76) Inventor: Franz Bencsits, Klosterneuburg (AT)

( * ) Notice: Subject to any disclaimer, the term of this patent is extended or adjusted under 35 U.S.C. 154(b) by 1554 days.

(21) Appl. No.: 10/533,218

(22) PCT Filed: Oct. 30, 2003

(86) PCT No.: PCT/EP03/12105
§ 371 (c)(1),
(2), (4) Date: Jun. 29, 2005

(87) PCT Pub. No.: WO2004/039158
PCT Pub. Date: May 13, 2004

(65) Prior Publication Data
US 2005/0249767 A1    Nov. 10, 2005

(30) Foreign Application Priority Data

Oct. 31, 2002 (DE) .................................. 102 50 898

(51) Int. Cl.
*A01N 31/14* (2006.01)
*A01N 25/00* (2006.01)

(52) U.S. Cl.
USPC .......................................... 514/722; 424/405

(58) Field of Classification Search
None
See application file for complete search history.

(56) References Cited

U.S. PATENT DOCUMENTS

| 4,774,081 | A | * | 9/1988 | Flashinski et al. ............. 514/617 |
| 4,832,059 | A | | 5/1989 | Garrard et al. |
| 6,087,402 | A | | 7/2000 | Zocchi et al. |
| 6,239,087 | B1 | * | 5/2001 | Mao et al. .................... 510/101 |
| 2002/0068075 | A1 | | 6/2002 | Tanaka et al. |

FOREIGN PATENT DOCUMENTS

| BR | 9 805 367 A | 6/2000 |
|----|----|----|
| DE | 143 023 | 7/1980 |
| DE | 101 01 336 A1 | 7/2002 |
| GB | 2 140 421 A | 11/1984 |
| JP | 02032035 A | 2/1990 |
| JP | 07112907 A | 5/1995 |
| JP | 10087407 | 4/1998 |
| WO | WO 92/02136 | 2/1992 |
| WO | WO 97/34986 | 9/1997 |
| WO | WO 00/19822 | 4/2000 |
| WO | WO 0019822 A1 * | 4/2000 |
| WO | WO 01/17345 A1 | 3/2001 |
| WO | WO 02/055648 A1 | 7/2002 |

OTHER PUBLICATIONS

Flashinski et al., Eur. J. Inorganic Chem., 1998, 11, 1739-1744.*
Acylic terpene, System of Nomenclature for Terpene Hydrocarbons, Chapter 2, pp. 12-14, 1955.*
International Search Report for PCT/EP03/12105 dated Mar. 18, 2004.
Taylor et al., "Diastereomers of the Insect Repellent 3-acetyl-2-(2',6'-dimethyl-5'-heptenyl)oxazolidine," Canadian Journal of Chemistry, vol. 62, Apr. 1984 (pp. 96-100).
Matsubara et al., "Synthesis of New Acetals and Their Derivatives from Terpene Aldehyde and Alcohol," Yuki Gosei Kagaku Kyokaisha, vol. 28, No. 8, 1970 (pp. 849-852) Abstract only.
Gualtieri et al., "Topical Mosquito Repellents IV: Alicyclic, Bicyclic, and Unsaturated Acetals, Aminoacetals, and Caboxamide Acetals," Journal of Pharmaceutical Sciences, vol. 61, No. 4, Apr. 1972 (pp. 577-580).

* cited by examiner

*Primary Examiner* — Kyle Purdy
(74) *Attorney, Agent, or Firm* — Kilyk & Bowersox, P.L.L.C.

(57) ABSTRACT

This invention relates to a new type of insect repellent which contains an acetal as the active component.

32 Claims, 10 Drawing Sheets

ACETALS AS INSECT REPELLANT AGENTS

This application is a National Stage Application of PCT/EP2003/012105, filed Oct. 30, 2003, which claims priority from German Patent Application No. 102 50 898.4, filed Oct. 31, 2002.

This invention relates to an insect repellent to repel flying, stinging, biting and sucking insects as well as pests of the genus Acarina (mites and ticks).

DESCRIPTION OF THE STATE OF THE ART

Insect repellents are chemical substances which have a repelling or destructive effect on insects and Acarina. Of great practical importance is their use in human and veterinary hygiene where they protect persons and animals from attack by blood-sucking, stinging, biting pests which are not just annoying, but are also potential carriers of diseases (malaria, spring-summer encephalitis, Lyme disease and many others). With insect repellents which are applied directly to the skin, it is necessary that they are compatible with the skin, non-toxic, proof against sweat and light and that there are no problems with regard to cosmetics (do not affect the skin, do not cause drying or wrinkles when applied externally) and pharmacological health aspects (irritation, penetration of deeper skin layers and in the blood and lymph circulation). In addition the protection of the skin sections to be treated or the protection of persons and animals due to treated objects in the surroundings should be retained as long as possible and the effective spectrum of the insect repellents should be as large as possible, i.e. they should be effective against as many different pests as possible.

In the past and to a lesser degree to the present time distilled oils, such as citronellol and lemon grass oil, as well as cloves oil, lavender oil, and eucalyptus oil and camphor have and are used as repellents, but which however all exhibit severe disadvantages, such as for example:

- questionable contents, such as eugenol in cloves oil, which in animal experiments has been found to be a carcinogen, mutagen and a skin-irritant or cineole in oil from Eucalyptus globulus, which, when applied to the skin, is able to cause strongly irritating exanthema;
- only short-term effectiveness, because the distilled oils evaporate quickly due to the body temperature of the skin surface and consequently frequent follow-up treatment is necessary to ensure protection;
- completely lacking resistance to light and consequently there is the permanent risk of photosensitization and product modification already before application.

In the recent past these compounds have therefore largely been superseded by so-called synthetic repellents. In the state of the art applied synthetic repellents are, for example, phthalic acid dimethylester, 1,2-ethylhexane-1,3-diol, 3,4-dihydro-2,2-dimethyl-4-oxo-2H-pyran-6-carboxylic acid n-butylester, succinic acid dipropylester, N,N-diethyl-3-methyl-benzamide (DEET—also N,N-diethyl-m-toluamide) and pyridine-2,5-dicarboxylic acid di-n-propylester (Ullmanns Encyclopädie der techn. Chemie, 4th edition, Vol. 13, p. 237 ff., 1977). Recently, hydroxyethylbutylpiperidine carboxylate [1-piperidine carboxylic acid-2-(2-hydroxyethyl)-1-methylpropylester] has been used increasingly.

Often however, these synthetic repellents are not resistant to sweat, irritate the mucous membranes and are also able to penetrate the uppermost layer of the skin, accumulating in the body, whereby the side effects resulting from this have not yet been completely researched, but there is a justified suspicion of toxic effects.

OBJECT OF THE INVENTION

Accordingly, the object of this invention is to provide an effective insect repellent for application directly onto the skin and/or the clothes and/or other objects and materials (bed linen, tent awnings, table cloths, etc.) surrounding the user requiring protection from annoying, harmful or disease-carrying stings and bites from insects and acarids (in particular ticks), based on natural raw substances or substances identical to natural substances, with the lowest toxicological risks, which in addition develops a high effectiveness over as long a time period as possible.

BRIEF DESCRIPTION OF THE INVENTION

This object is solved according to the invention by an insect repellent according to claim 1 or by the use according to claim 2. Preferred embodiments are given in the sub-claims. The basic structure of the substances according to the invention is an acyclic terpene with ten carbon atoms, i.e. a monoterpene, preferably singly or doubly unsaturated. The organic groups forming the acetal or semi-acetal are termed in the following as acetal or semi-acetal radicals.

The following description explains this invention in more detail by reference to the insect repellent according to the invention. These comments also apply in equivalent form to the claimed usage.

The effectiveness of the compounds according to the invention is based on their capacity of forming a fully covering, long-lasting film on the skin, which reliably prevents the substances or signals (sweat, $CO_2$, uric and butyric acids, body heat) essential for the location of suitable objects of prey (people and mammals) being released from the skin for biting and stinging, blood-sucking pests, so that a warm-blooded object treated with the compounds according to the invention can no longer be identified and is therefore not subject to attack. With contact or direct action the agent according to the invention has a mortal effect due to the properties of the insect repellent according to the invention in that the chitin layer of the pests is modified and fluid is forced from their bodies. These direct actions are of an essential purely physical nature, so that the development of resistances, as inevitably occurs with chemically or biochemically effective substances due to the rapid alternation of generations and thus the rapid passing of the appropriate genetic information to the descendants is eliminated with the substances employed according to the invention. The use according to the invention of the substances quoted in this application ensures a good insect repellent effect. The application can either take place directly on the skin of the individual to be protected (person or animal) or also to the clothing or other articles, such as bed linen, etc.

DETAILED DESCRIPTION OF THE INVENTION

Figures 1, 2, 3, 4, 5, 6, 7, 7B:
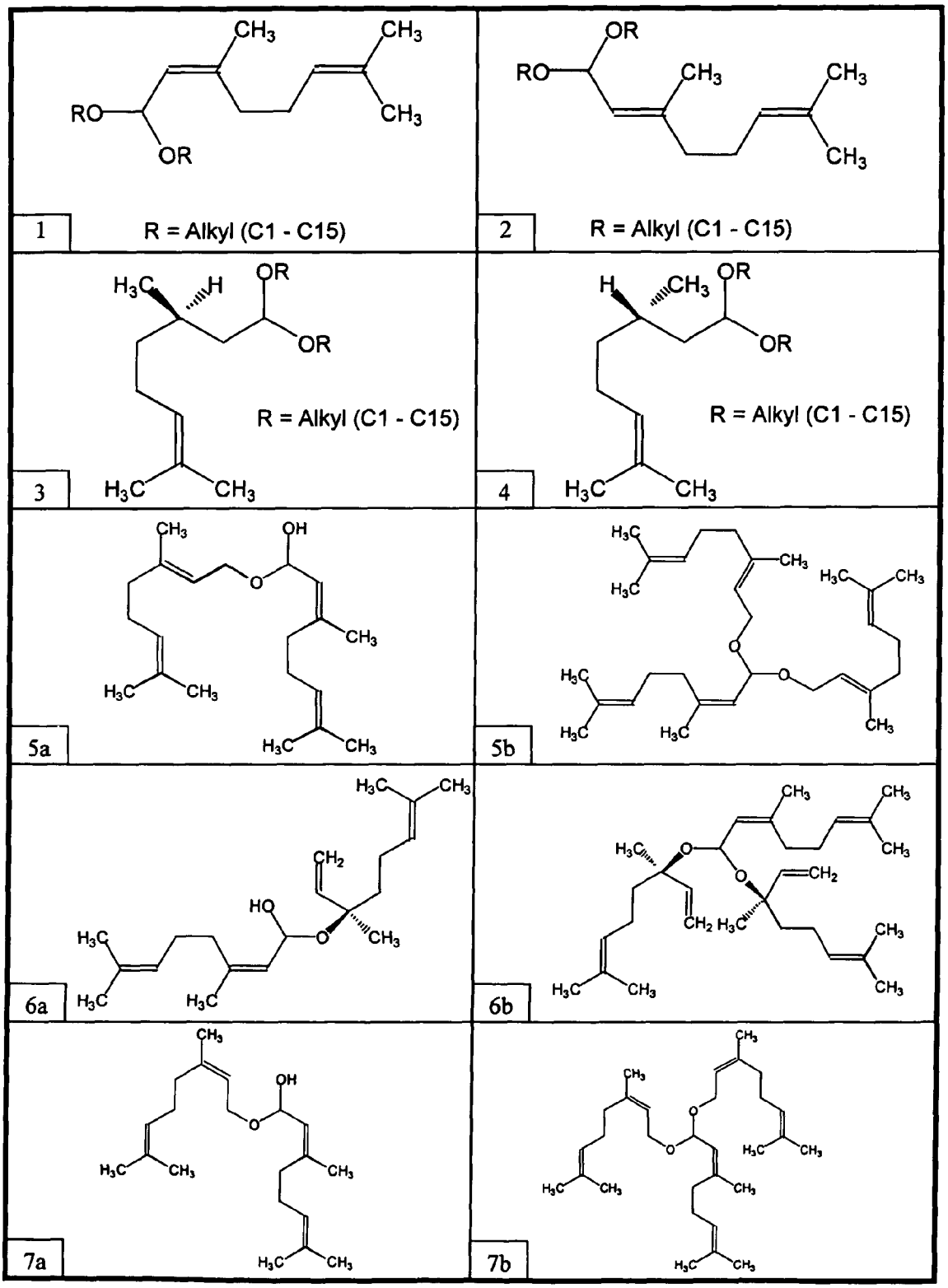
FIGS. 1 to 63 show the chemical composition of some of the compounds quoted in the description, which are particularly preferred in the practice of this invention.
Figures 8, 8A, 9, 10, 11, 12, 12B:
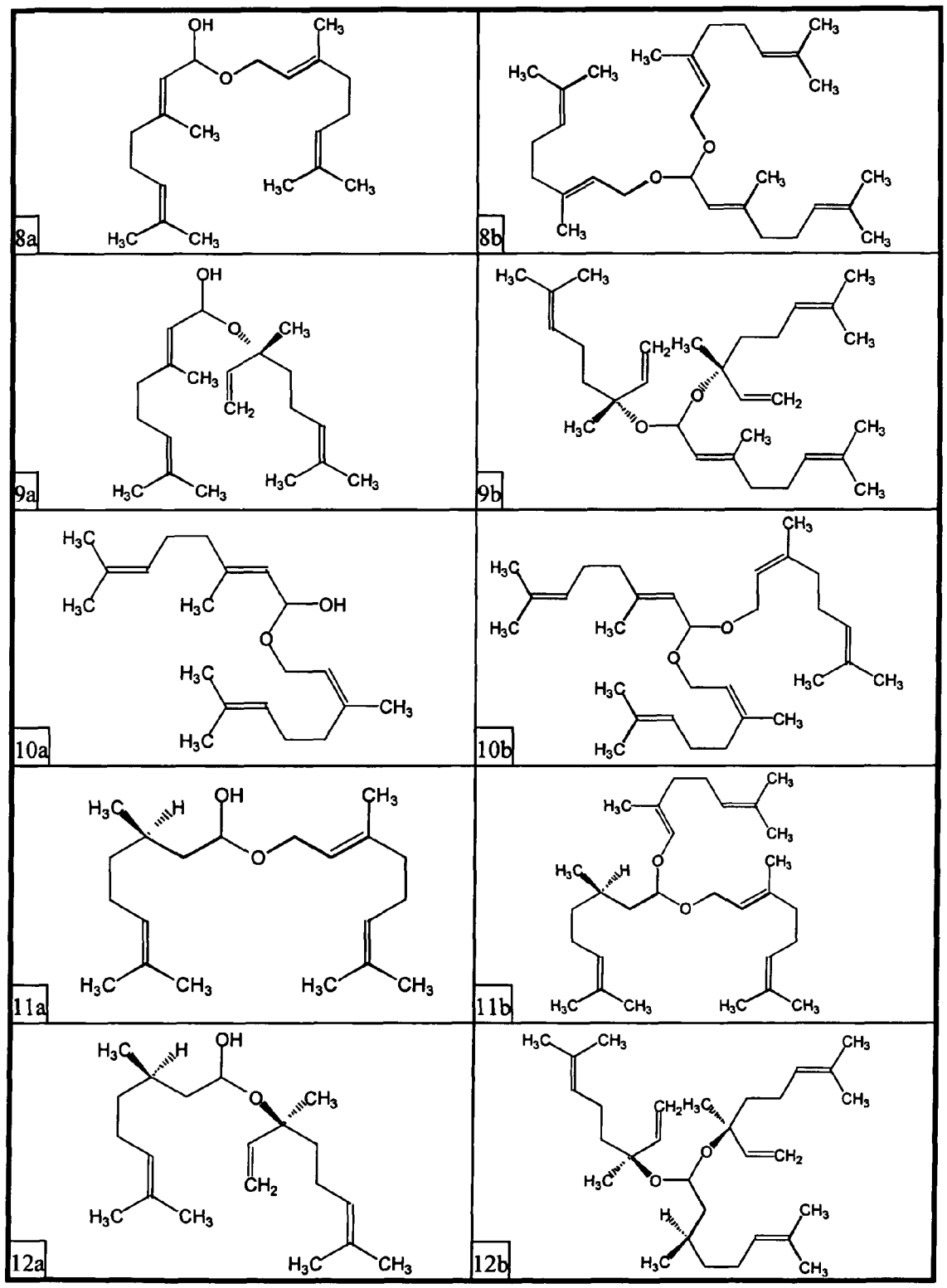
Figures 13, 13A, 14, 15, 16, 17, 17B:
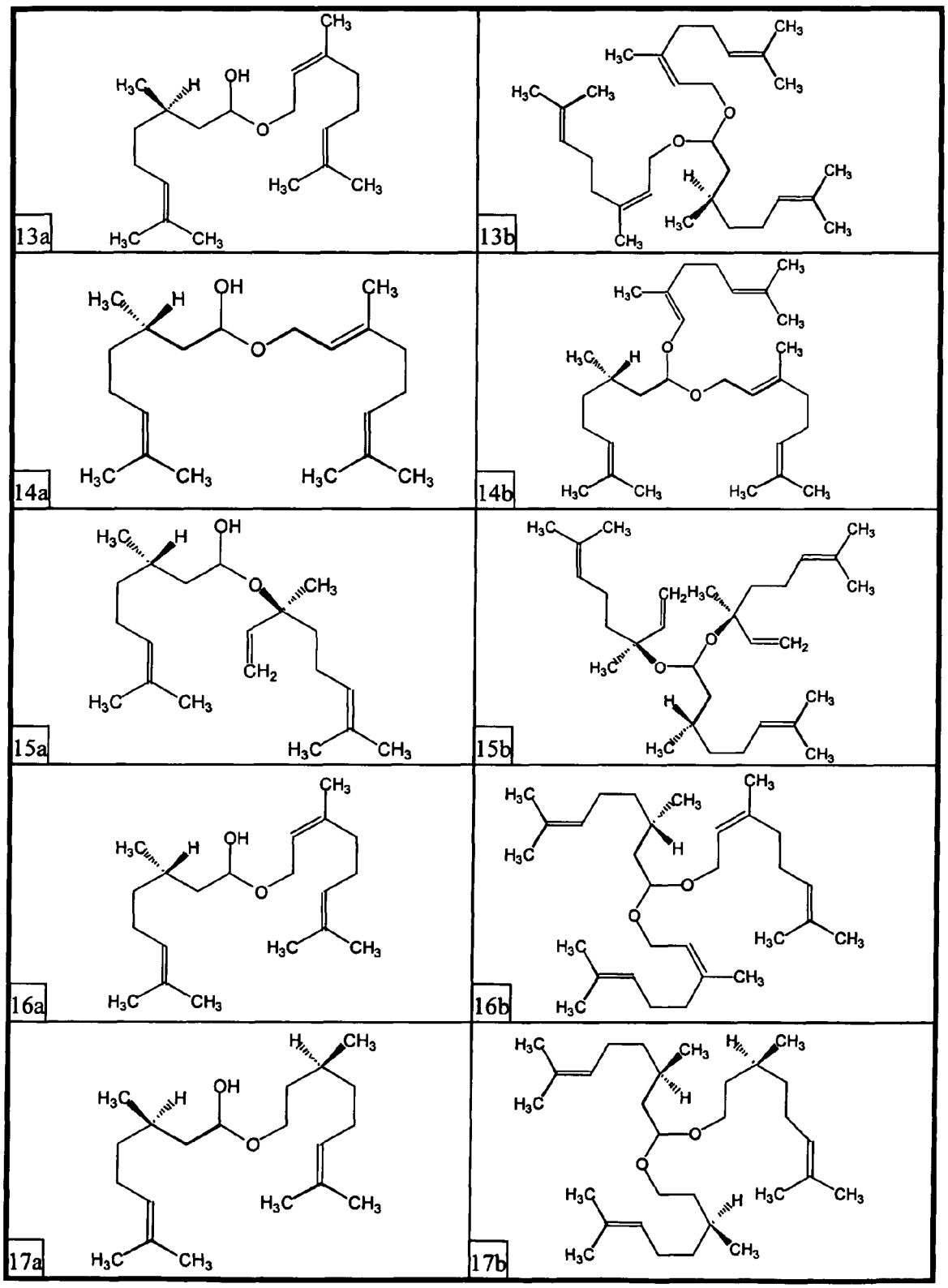
Figures 18, 18A, 19, 20, 21, 22, 22B:
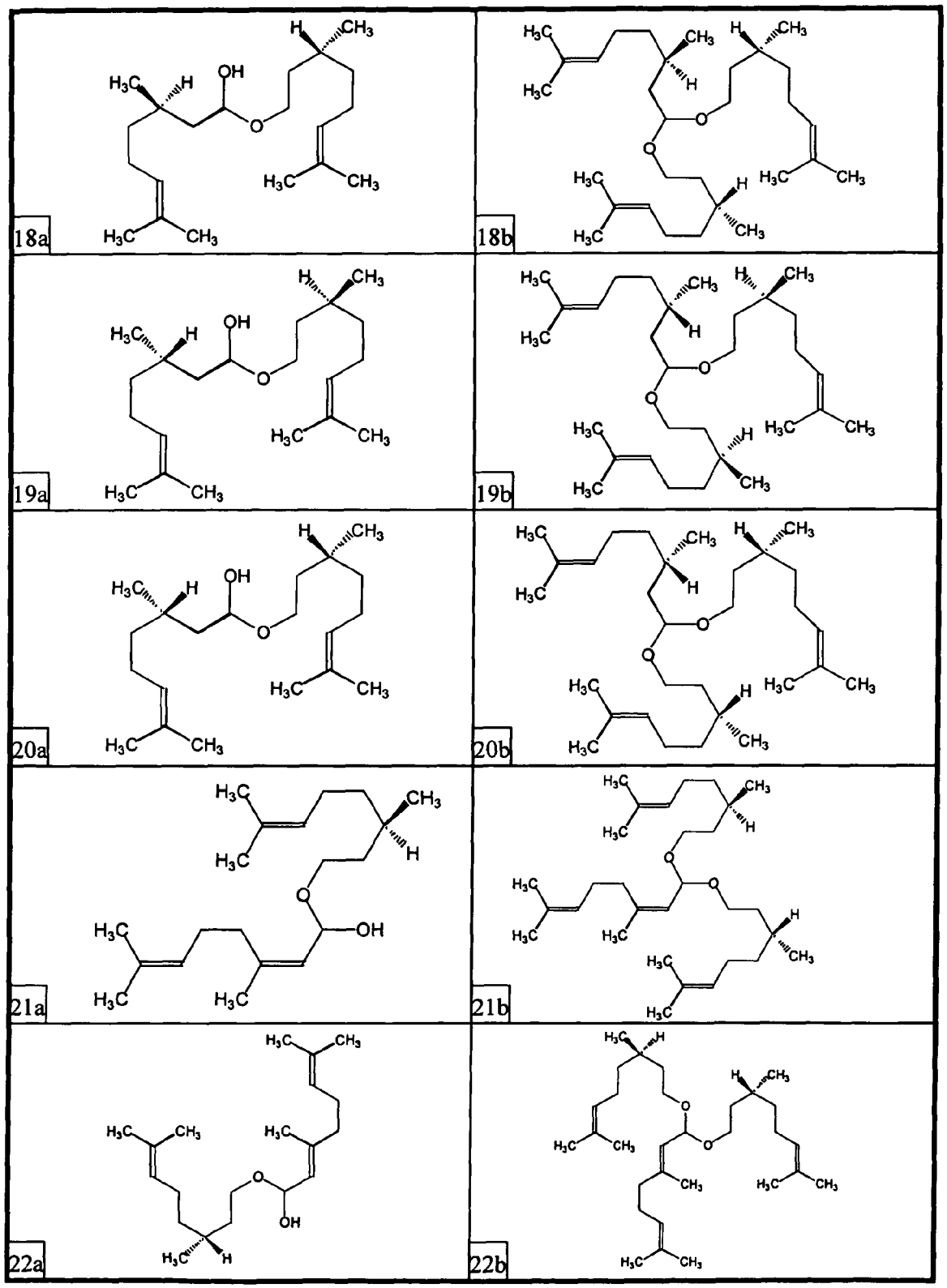
Figures 23, 23A, 24, 25, 26, 27, 27B:
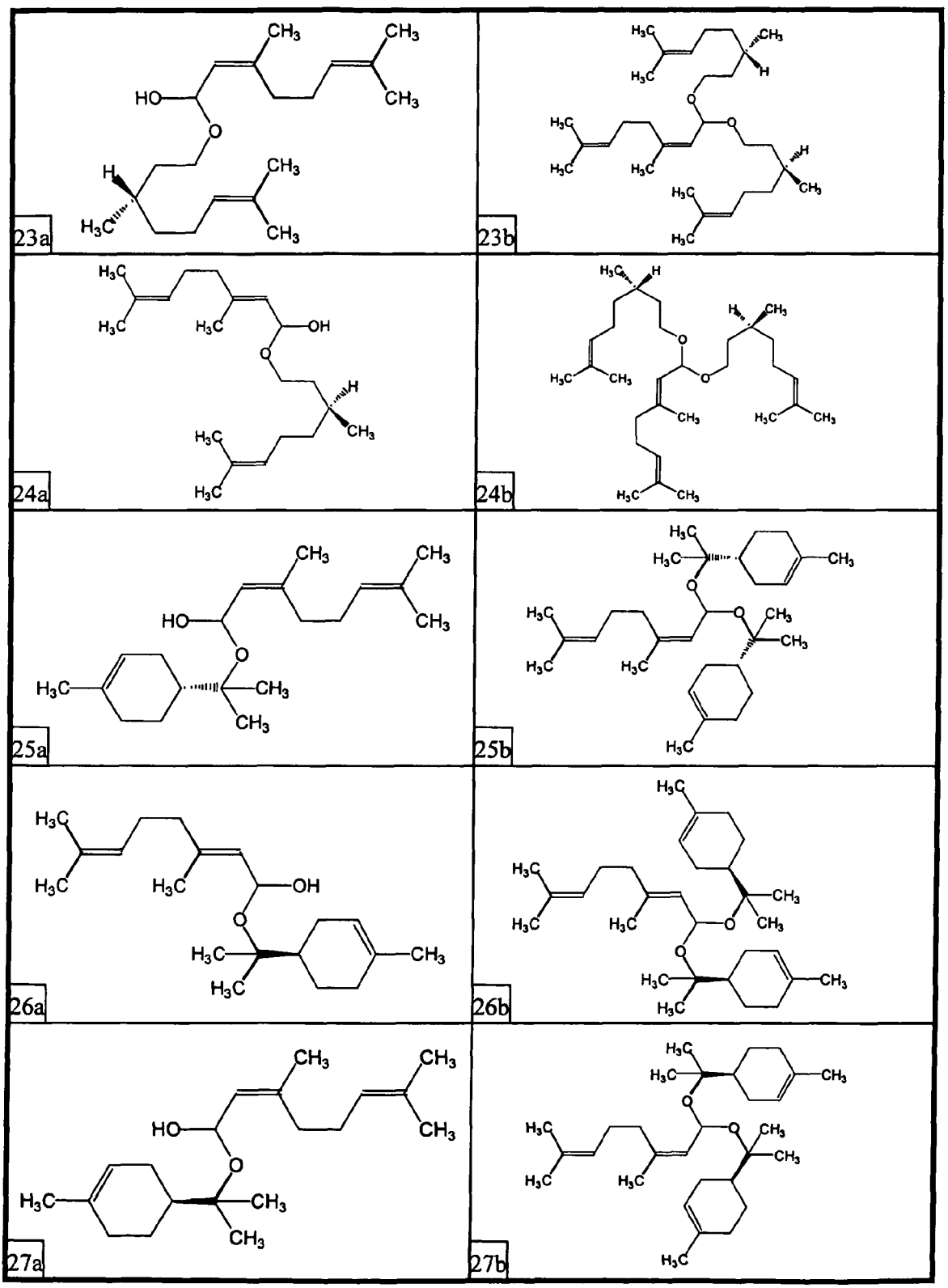
Figures 28, 28A, 29, 30, 31, 32, 32B:
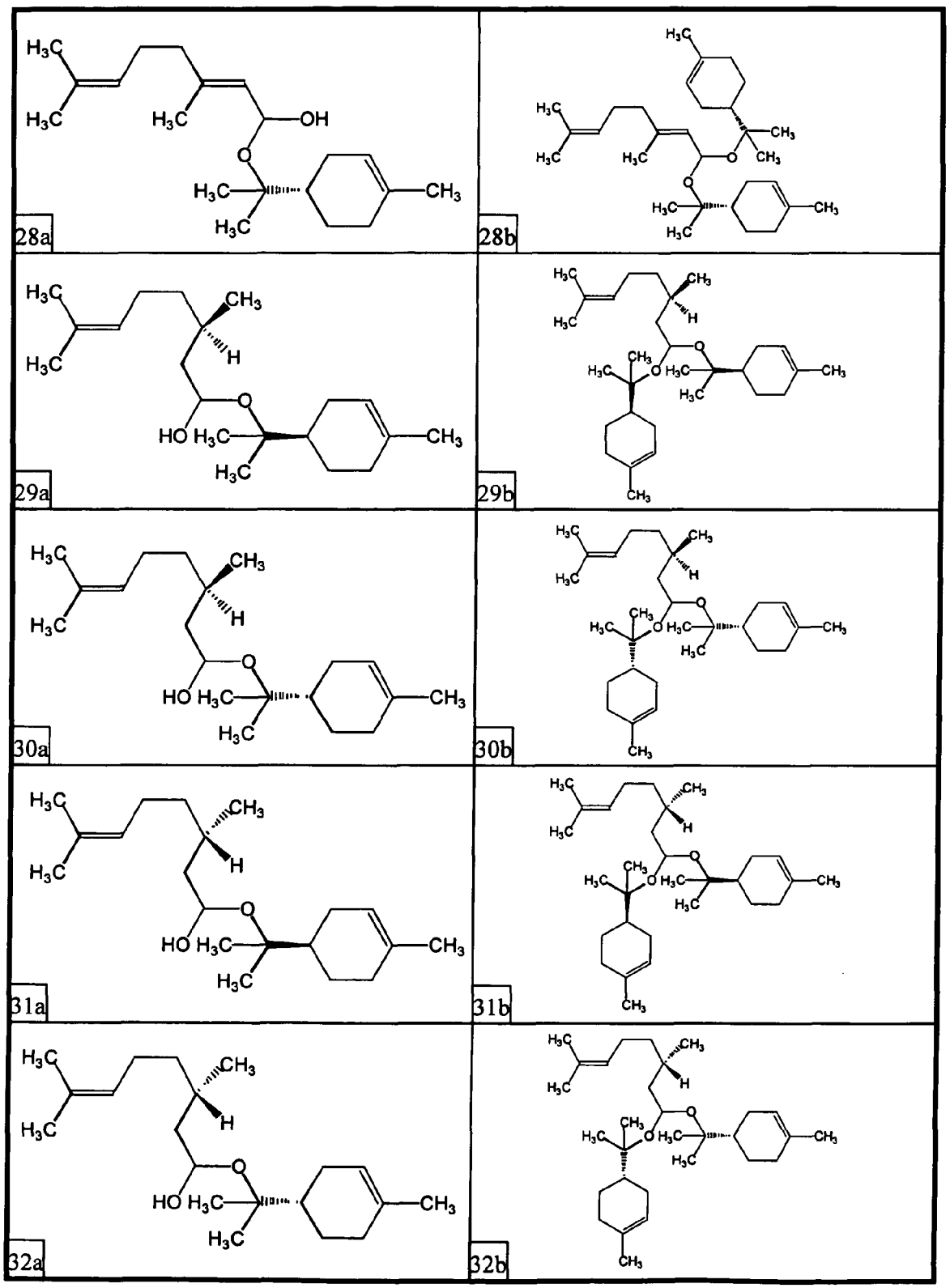
Figures 33, 34, 35, 36, 37, 38, 39, 40, 41, 42:
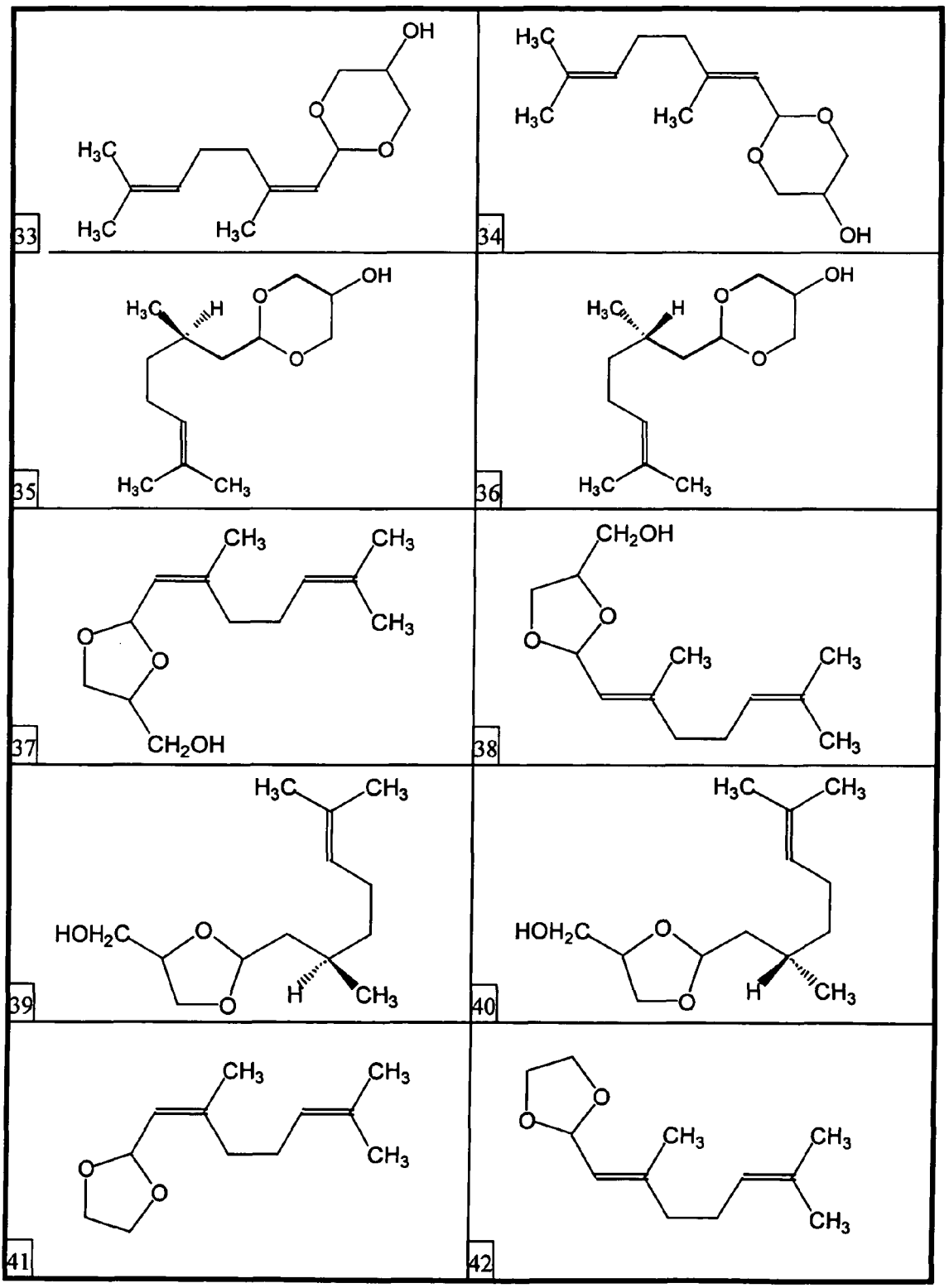
Figures 43, 44, 45, 46, 47, 48, 49, 50, 51, 52:
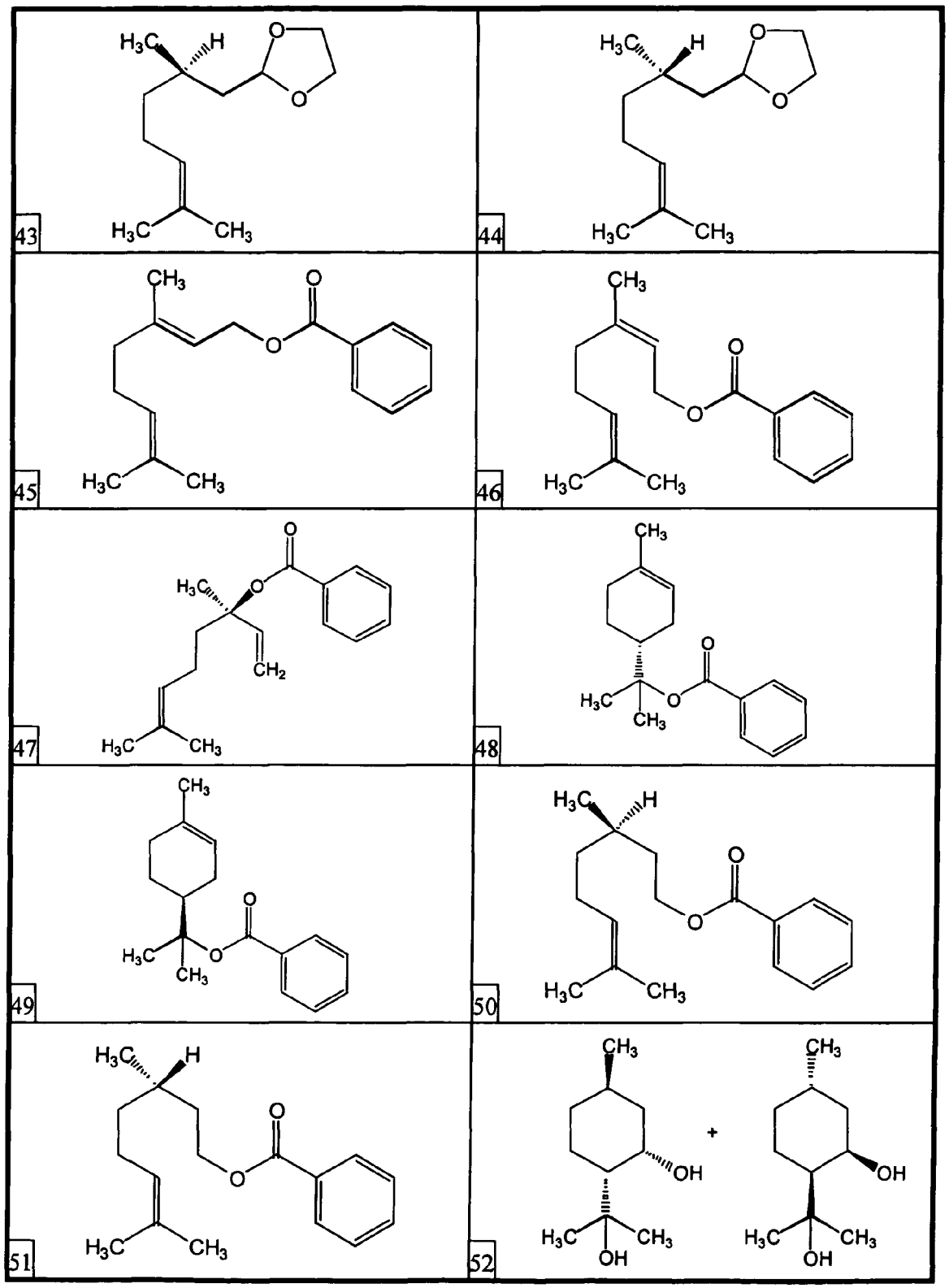
Figures 53, 54, 55, 56, 57, 58, 59, 60, 61, 62:
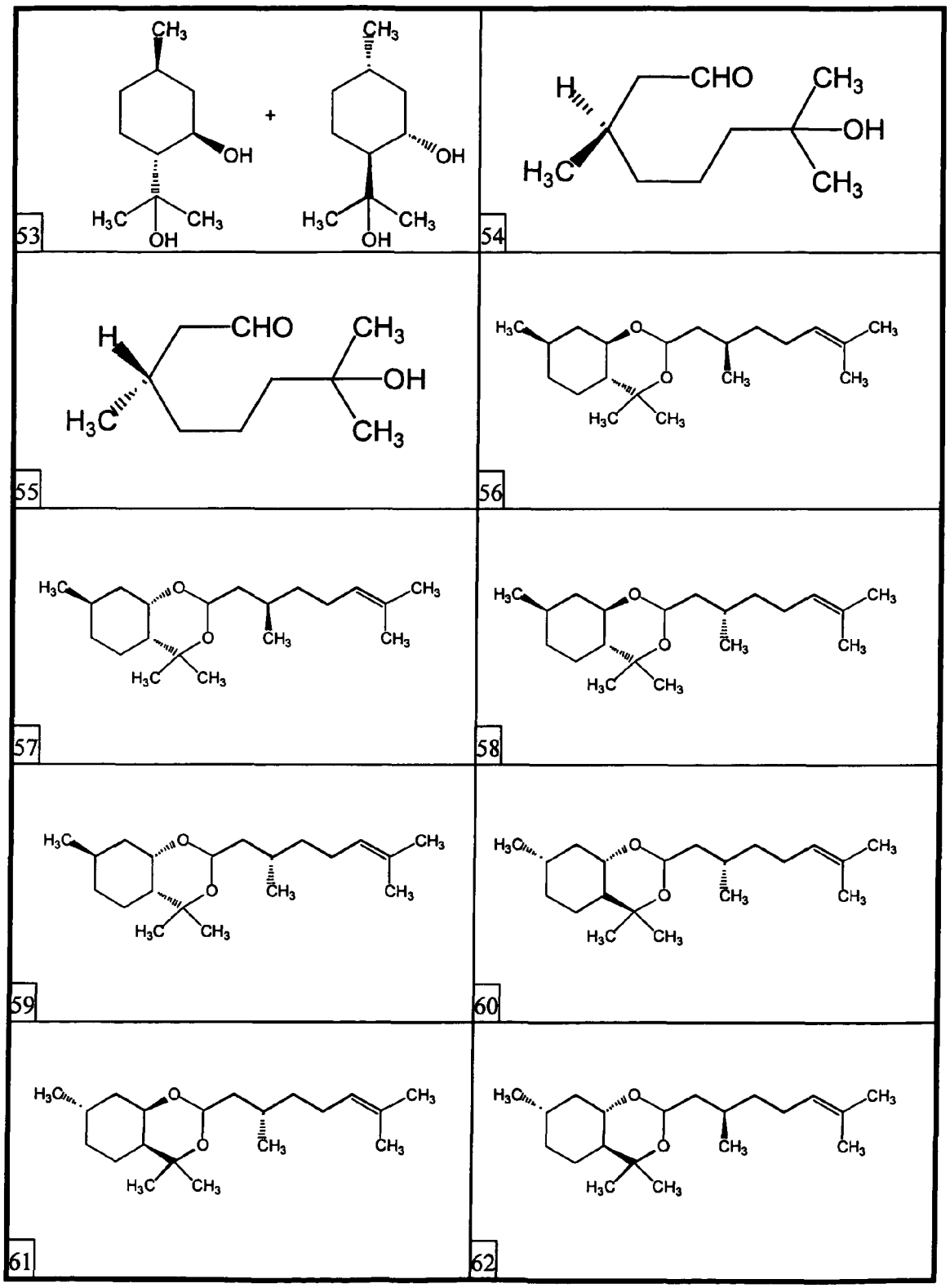
Figure 63:
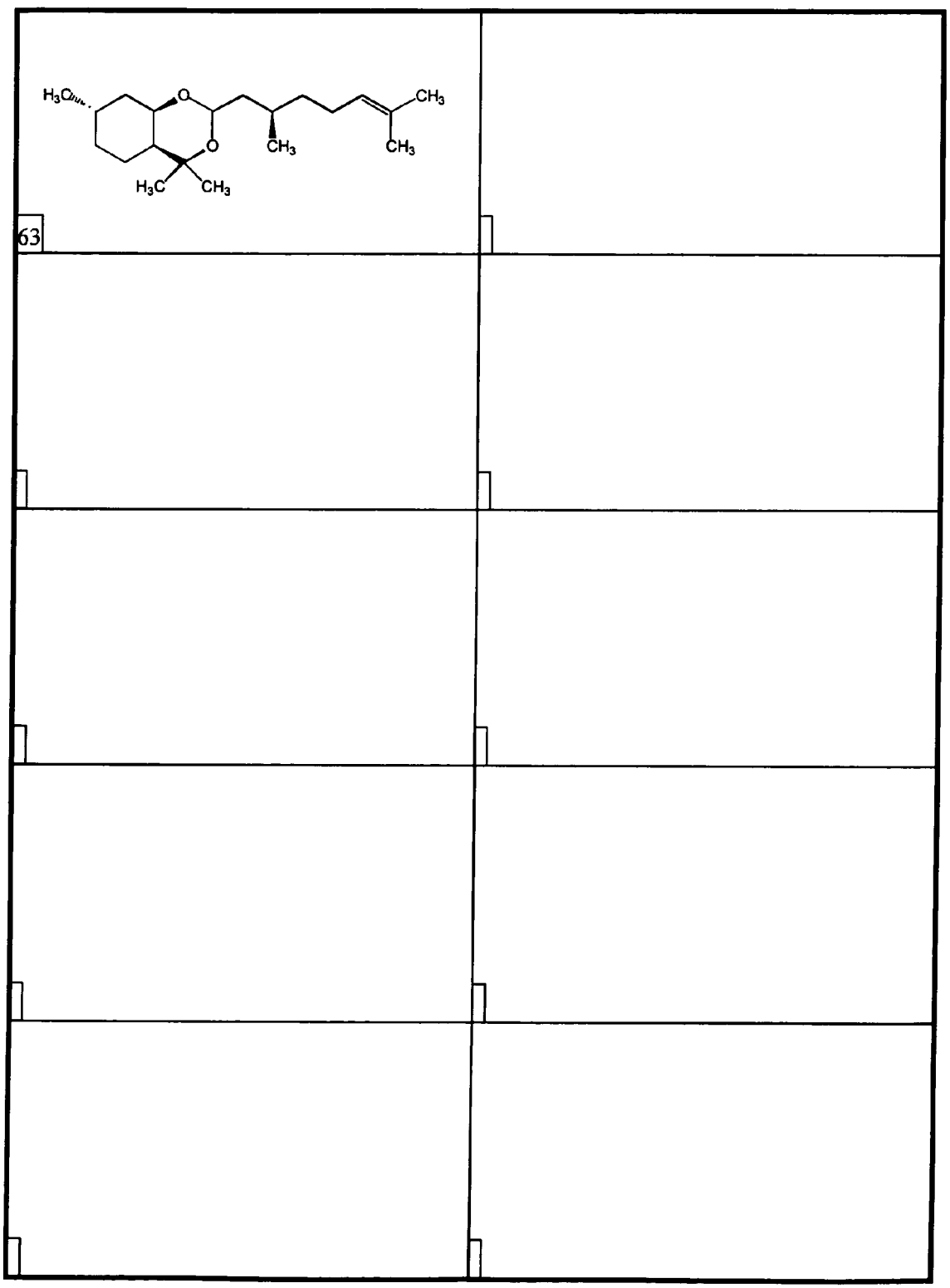

The substances according to the invention which are used as an insect repellent, such as for example the following preferred substances

| | |
|---|---|
| Octadienal dialkylacetal, | Octenal dialkylacetal, |
| Octadienal octadienyl acetal, | Octenal octadienyl acetal, |
| Octenal octenyl acetal, | Octadienal octenyl acetal, |
| Octadienal-p-menthenyl acetal, | Octenal-p-menthenyl acetal, |
| 2-heptadienyl-1,3-dioxane, | 2-heptadienyl-1,3-dioxol, |
| 2-heptenyl-1,3-dioxane and | 2-heptenyl-1,3-dioxol | can be directly procured if they are commercially available or they can be produced from the following compounds, whereby the principal reaction steps are known to the person skilled in the art:

Constituents of natural distilled oils or their synthetically manufactured substitutes, such as:
- neral and geranial [3,7-dimethyl-2,6-octadienal],
- (+)-citronellal, (−)-citronellal [3,7-dimethyl-6-octenal],
- geraniol [(E)-3,7-dimethyl-2,6-octadien-1-01],
- linalool [3,7-dimethyl-6-octadien-3-ol],
- nerol [(Z)-3,7-dimethyl-2,6-octadien-1-ol],
- (+)-citronellol, (−)-citronellol [3,7-dimethyl-6-octen-1-ol] and
- (+)-terpineol, (−)-terpineol [p-menthane-1,8-diol]), which are reacted amongst themselves and also using mono- or multivalent, primary, secondary or tertiary, straight chained, branched, saturated or unsaturated alcohols with one to fifteen C atoms according to methods described below to the respective acetals.

Organic or inorganic acids are used as catalysts.

Preferred acetals are those whose acetal groups are formed symmetrically by alkyl groups with one to fifteen carbon atoms, more preferably with one to twelve carbon atoms. The quoted carbon atom numbers also apply to the semi-acetals.

The compositions according to the invention can contain other substances such as: saturated or unsaturated, aliphatic carboxylic acids with one to twelve carbon atoms, preferably octanoic acid or decanoic acid, benzoic acid ester, p-mentha-3,8-diols, hydroxyoctanals, p-mentha-3,8-diylacetals.

Preferred compositions according to the invention contain:
0.02 to 95.00% wt. of one or more of the substances according to the invention, preferred structures 1 to 44 (in the following (I)),
0.00 to 95.00% wt. of a natural or synthetic fatty oil in which the substances according to the invention are soluble, preferably coconut oil (in the following (II)),
0.02 to 50.00% wt. of one or more saturated or unsaturated, aliphatic carboxylic acids with 1 to 12 carboxylic atoms, preferably octanoic or decanoic acid (in the following (III)),
0.02 to 50.00% wt. of one or more benzoic acid esters preferably with the Structure 45 to 51 (in the following (IV)),
0.00 to 50.00% wt. of p-mentha-3,8-diol, preferably with the Structure 52 or 53 (in the following (V)),
0.00 to 50.00% wt. of hydroxyoctanal preferably with the Structure 54 to 55 (in the following (VI)),
0.00 to 20.00% wt. of one or more diylacetals, preferably with the Structure 56 to 59 (in the following (VII)),
0.00 to 50.00% wt. of one or more emulsifiers, preferably lecithin, PEG derivatives of castor oil and/or decylglucoside (in the following (VIII),
0.00 to 99.88% wt. of water (in the following (IX)).

More preferably a composition according to the invention contains:
0.02 to 30.00% wt. of I
0.05 to 30.00% wt. of III
0.08 to 30.00% wt. of IV
5.00 to 30.00% wt. of V
0.05 to 10.00% wt. of VII
0.05 to 10.00% wt. of VIII
5.00 to 99.88% wt. of IX Especially preferably a composition according to the invention contains:
0.02 to 16.00% wt. of I
0.05 to 20.00% wt. of III
0.08 to 10.00% wt. of IV
0.05 to 10.00% wt. of VIII
44.00 to 99.88% wt. of IX The insect repellents according to the invention can be incorporated into the following types of finished products to give the consumer a choice in the form of the applied products:

Emulsion, dispersion, lotion, cream, gel or solution.

All the usual methods of preparation can be used for the manufacture of these forms of application.

Similarly, the usual basic materials and additives can be used. These comprise solvents, solvent accelerators, solubilisers, emulsifiers, wetting agents, anti-foaming agents, halogens, buffers, gel and film promoters, thickening, binding and lubricating agents, greasing agents, spreading agents, anti-sticking and flow regulation agents, moisture retention and drying agents, acid and alkali pH regulators, such as organic acids and fruit acids or hydroxides of earthy base metals, amines und amides, fillers and auxiliary substances, such as antioxidants, preservatives, odour adjusters and colorants, which are usually used for chemical-technical, cosmetic and pharmaceutical preparations.

The term "emulsion" comprises all dispersive systems of two or more liquids mutually immiscible, whereby the emulsion components may also be present at room temperature as solids or amorphous and crystalline waxes. These emulsions may be macro or micro-emulsions. Typically water-in-oil and/or oil-in-water emulsions are used. Emulsifiers are used to reduce the interfacial work (work to be applied in emulsifying). Emulsifiers are normally interfacially active substances, typically with hydrophilic end groups. Typical examples of these comprise:
- anionic emulsifiers, i.e. emulsifying agents with carboxylate, sulphonate, phosphate, polyphosphate, lactate, citrate, tartrate, glucose or polyglucose end groups;
- cationic emulsifiers, i.e. emulsifiers with amine salts or quaternary ammonia end groups;
- amphoteric and zwitter ionic emulsifiers, i.e. emulsifiers with zwitter ionic or betaine end groups, as well as
- non-ionic emulsifiers, i.e. emulsifiers with alcohol, polyether, glycerine, sorbit, pentaerythrite, saccharose, acetic acid and/or lactic acid radicals in the end group.

All emulsifiers contain in addition lipophilic end groups, such as alkyl or alkyl radicals, appropriately straight chained, branched or cyclic, as well as aryl and alkylaryl radicals. Furthermore hydrophilic side groups can be included such as hydroxyl, ester, sulphamide, amide, amine, polyamide, polyamine, ether, polyether, glycerine, sorbit, penta-erythrite or saccharose groups.

The term "gels" comprises dimensionally stable, easily deformable systems, rich in liquids, of at least two components. Normally these two components are: a) a liquid and b) a solid, colloidally distributed substance, such as gelatine, silicic acid, montmorillonite, bentonite, polysaccharides, polyacrylates, pectins and many more.

The methods for the manufacture of all insect repellents according to the invention can be carried out in any production facility equipped for the production of chemicals without special technical effort.

The Following Examples are Quoted as Typical Methods:

The constituents are stirred in an aqueous solution for 2 to 15 hours at 50° C. to 150° C. in a suitable, tightly sealed stainless steel vessel with a minimum quality of V4A with permanent stirring mechanism and heating.

The pure acetals are powders or crystalline, but fat-dispersing substances so that use in a pure form as insect repellent for the skin is difficult. Coconut oil has proven to be a good dispersion agent. The addition of the foodstuff emulsifier lecithin can be used for the production of aqueous solutions.

The following compositions were produced by suitable mixing of the quoted compounds:

IAM 1=95.00% wt. Structure 1+5.00% wt. coconut oil
IAM 2=5.00% wt. Structure 1+95.00% wt. coconut oil
IAM 3=50.00% wt. Structure 1+15.00% wt. coconut oil+10.00% wt. lecithin+25.00% wt. water
IAM 4=50.00% wt. Structure 2, ditto
IAM 5=50.00% wt. Structure 3, ditto
IAM 6=50.00% wt. Structure 4, ditto
IAM 6=50.00% wt. Structure 5a, ditto
IAM 7=50.00% wt. Structure 5b, ditto
IAM 8=50.00% wt. Structure 6a, ditto
IAM 9=50.00% wt. Structure 6b, ditto
IAM 10=50.00% wt. Structure 7a, ditto
IAM 11=50.00% wt. Structure 7b, ditto
IAM 12=50.00% wt. Structure 8a, ditto
IAM 13=50.00% wt. Structure 8b, ditto
IAM 14=50.00% wt. Structure 9a, ditto
IAM 15=50.00% wt. Structure 9b, ditto
IAM 16=50.00% wt. Structure 10a, ditto
IAM 17=50.00% wt. Structure 10b, ditto
IAM 18=50.00% wt. Structure 11a, ditto
IAM 19=50.00% wt. Structure 11b, ditto
IAM 20=50.00% wt. Structure 12a, ditto
IAM 21=50.00% wt. Structure 13a, ditto
IAM 22=50.00% wt. Structure 14a, ditto
IAM 23=50.00% wt. Structure 14b, ditto
IAM 24=50.00% wt. Structure 15a, ditto
IAM 25=50.00% wt. Structure 15b, ditto
IAM 26=50.00% wt. Structure 33, ditto
IAM 27=50.00% wt. Structure 34, ditto
IAM 28=50.00% wt. Structure 35, ditto
IAM 29=50.00% wt. Structure 36, ditto
IAM 30=50.00% wt. Structure 37, ditto
IAM 31=50.00% wt. Structure 38, ditto
IAM 32=50.00% wt. Structure 39, ditto
IAM 33=50.00% wt. Structure 40, ditto
IAM 34=50.00% wt. Structure 41, ditto
IAM 35=50.00% wt. Structure 42, ditto
IAM 36=50.00% wt. Structure 43, ditto
IAM 37=50.00% wt. Structure 44, ditto
IAM 38=25.00% wt. Structure 16a+25.00% wt. Structure 20b+15.00% wt. coconut oil+10.00% wt. lecithin+25.00% wt. water
IAM 39=25.00% wt. Structure 16b+25.00% wt. Structure 20a, ditto
IAM 40=25.00% wt. Structure 22a+25.00% wt. Structure 28a, ditto
IAM 41=25.00% wt. Structure 22b+25.00% wt. Structure 28b, ditto
IAM 42=25.00% wt. Structure 2+25.00% wt. Structure 42, ditto Since acetals dissolve in esters, the addition of coconut oil could be omitted.

IAM 43=40.00% wt. Structure 2+10.00% wt. Structure 45+10.00% wt. lecithin+40.00% wt. water
IAM 44=40.00% wt. Structure 8a+10.00% wt. Structure 46, ditto
IAM 45=40.00% wt. Structure 14b+10.00% wt. Structure 47, ditto
IAM 46=40.00% wt. Structure 16a+10.00% wt. Structure 48, ditto
IAM 47=40.00% wt. Structure 17b+10.00% wt. Structure 50, ditto
IAM 48=30.00% wt. Structure 2+10.00% wt. Structure 45+10.00% wt. octanoic acid+10.00% wt. lecithin+40.00% wt. water
IAM 49=30.00% wt. Structure 8a+10.00% wt. Structure 46, ditto
IAM 50=30.00% wt. Structure 14b+10.00% wt. Structure 47, ditto
IAM 51=30.00% wt. Structure 1+10.00% wt. Structure 51, ditto
IAM 52=30.00% wt. Structure 5a+10.00% wt. Structure 49, ditto
IAM 53=30.00% wt. Structure 42+10.00% wt. Structure 48, ditto
IAM 54=20.00% wt. Structure 2+10.00% wt. Structure 45+10.00% wt. Structure 52+10.00% wt. octanoic acid+10.00% wt. lecithin+40.00% wt. water
IAM 55=20.00% wt. Structure 8a+10.00% wt. Structure 46, ditto
IAM 56=20.00% wt. Structure 14b+10.00% wt. Structure 47, ditto
IAM 57=20.00% wt. Structure 1+10.00% wt. Structure 51, ditto
IAM 58=20.00% wt. Structure 5a+10.00% wt. Structure 51, ditto
IAM 59=20.00% wt. Structure 2+10.00% wt. Structure 45+10.00% wt. Structure 53+10.00% wt. octanoic acid+10.00% wt. lecithin+40.00% wt. water
IAM 60=20.00% wt. Structure 8a+10.00% wt. Structure 46, ditto
IAM 61=20.00% wt. Structure 14b+10.00% wt. Structure 47, ditto
IAM 62=20.00% wt. Structure 1+10.00% wt. Structure 51, ditto
IAM 63=20.00% wt. Structure 5a+10.00% wt. Structure 51, ditto
IAM 64=20.00% wt. Structure 2+10.00% wt. Structure 45+5.00% wt. Structure 52+5.00% wt. Structure 5a+10.00% wt. octanoic acid+10.00% wt. lecithin+40.00% wt. water
IAM 65=20.00% wt. Structure 8a+10.00% wt. Structure 46, ditto
IAM 66=20.00% wt. Structure 14b+10.00% wt. Structure 47, ditto
IAM 67=20.00% wt. Structure 1+10.00% wt. Structure 51, ditto
IAM 68=20.00% wt. Structure 5a+10.00% wt. Structure 51, ditto
IAM 69=16.00% wt. Structure 2+10.00% wt. Structure 45+5.00% wt. Structure 52+5.00% wt. Structure 53+4.00% wt. Structure 56+10.00% wt. octanoic acid+10.00% wt. lecithin+40.00% wt. water
IAM 70=20.00% wt. Structure 8a+10.00% wt. Structure 46, ditto
IAM 71=20.00% wt. Structure 14b+10.00% wt. Structure 47, ditto
IAM 72=20.00% wt. Structure 1+10.00% wt. Structure 51, ditto
IAM 73=20.00% wt. Structure 5a+10.00% wt. Structure 51, ditto IAM 74=16.00% wt. Structure 2+10.00% wt. Structure 45+5.00% wt. Structure 52+5.00% wt. Structure 53+4.00% wt. Structure 56+10.00% wt. octanoic acid+10.00% wt. lecithin+40.00% wt. water IAM 75=20.00% wt. Structure 8a+10.00% wt. Structure 46, ditto IAM 76=20.00% wt. Structure 14b+10.00% wt. Structure 47, ditto IAM 77=20.00% wt. Structure 1+10.00% wt. Structure 51, ditto IAM 78=20.00% wt. Structure 5a+10.00% wt. Structure 51, ditto IAM 79=16.00% wt. Structure 2+10.00% wt. Structure 45+5.00% wt. Structure 52+5.00% wt. Structure 53+2.00% wt. Structure 58+2.00% wt.

Structure 59+10.00% wt. octanoic acid+10.00% wt. lecithin+40.00% wt. water

IAM 80=20.00% wt. Structure 8a+10.00% wt. Structure 46, ditto

IAM 81=20.00% wt. Structure 14b+10.00% wt. Structure 47, ditto

IAM 82=20.00% wt. Structure 1+10.00% wt. Structure 51, ditto

IAM 83=20.00% wt. Structure 5a+10.00% wt. Structure 51, ditto

IAM 84=5.00% wt. Structure 2+5.00% wt. Structure 45+5.00% wt. Structure 52+3.00% wt. Structure 53+2.00% wt. Structure 58+1.00% wt. Structure 59+5.00% wt. octanoic acid+5.00% wt. coconut oil+3.00% wt. PEG-40 hydrogenated castor oil+66.00% wt. water IAM 85=5.00% wt. Structure 8b+5.00% wt. Structure 48+5.00% wt. Structure 54+3.00% wt. Structure 56+2.00% wt. Structure 57+1.00% wt. Structure 59+5.00% wt. octanoic acid+5.00% wt. coconut oil+3.00% wt. PEG-40 hydrogenated castor oil+66.00% wt. water IAM 86=0.20% wt. Structure 1+0.80% wt. Structure 45+0.67% wt. decyl glucoside+98.33% wt. water IAM 87=0.80% wt. Structure 1+0.20% wt. Structure 45, ditto IAM 88=0.20% wt. Structure 8a+0.80% wt. Structure 45, ditto IAM 89=0.20% wt. Structure 5a+0.80% wt. Structure 45, ditto IAM 90=0.20% wt. Structure 2+0.40% wt. Structure 45+0.40% wt. octanoic acid+0.67% wt. decyl glucoside+98.33% wt. water IAM 91=0.02% wt. Structure 2+0.02% wt. Structure 45+0.02% wt. octanoic acid+0.06% wt. decyl glucoside+99.88% wt. water IAM 92=0.04% wt. Structure I+0.02% wt. Structure 46+0.02% wt. octanoic acid+0.06% wt. PEG-40 hydrogenated castor oil+99.86% wt. water IAM 93=0.02% wt. Structure 1+0.04% wt. Structure 46, ditto IAM 94=0.02% wt. Structure 3+0.04% wt. Structure 47, ditto

EXAMPLES

The compositions were tested with regard to their effectiveness as follows.

1. Series of Tests for Repellence Against Mosquitoes on People

The pest repellents according to examples IAM 1 to IAM 85 were each tested on various persons of all age groups, whereby a product on the market, regarded as extremely effective (KIK AKTIV®—with 30% DEET as active ingredient), was used as the reference.

The right lower arm of the respective test person was treated over an area of approx. 250 cm$^3$ with the appropriate test product (IAM 1 to 85). A quantity of 2 ml of the appropriate test substance was evenly spread over the test area. The treated surface of the lower arm was sealed off, both towards the upper arm and also towards the wrist, with an adhesive tape, sealed against mosquito bites, extending over a short plastic tube. The untreated hand was covered with a thick glove and was thus used at the same time as a control for the biting activity of the mosquitoes, because with the urge to bite they alighted on the glove and tried to bite through the material into the hand located underneath. The left lower arm was similarly treated with the reference product (REF). As experimental animals, about 300 to 400 female yellow fever mosquitoes were put into a breeding cage sized 40×40×40 cm for each single test (IAM on the right against REF on the left). This is a population density which hardly ever occurs naturally and consequently enables good differentiation of the effectiveness of the individual substances.

For the test the hand and the prepared lower arm were held, after a one-hour waiting period, in the cage for ten minutes every hour, first the left with REF and then the right with IAM and during this period the number of mosquitoes were noted, which (a) tried to bite through the glove (positive control),
(b) flew closer than 3 cm to the treated surface, but turned away again (remote protection effect),
(c) remained on the treated surface for longer than two seconds, but did not bite and
(d) bit into the treated skin and sucked blood.

Each test person was subjected to only one experiment each day in order to avoid the risk of product accumulation and any cross-reactions of the products on insufficiently cleansed skin.

Test Results:
Legends:
1=Time after the application of the respective test product in hours.
2=Exposure duration within the ten-minute test duration per hour; cancellation on biting and figures for the minutes of the resulting shortened exposure duration.
a=Mosquitoes resting on the glove.
b=Flying mosquitoes, which approached the treated surface closer than 3 cm and turned away again, without alighting and mosquitoes which remained alighted on the test surface for less than two seconds.
c=Mosquitoes which alighted on the treated surface for longer than two seconds, but which did not bite and which thus, together with the mosquitoes of Criterion b, form the annoyance factor.
d=Number of biting mosquitoes before the cancellation of the test.

| 1 Product | 2 | a IAM 1 | b | c | d | a IAM 2 | b | c | d | a IAM 3 | b | c | d | a IAM 4 | b | c | d |
|---|---|---|---|---|---|---|---|---|---|---|---|---|---|---|---|---|---|
| 1 | 10 | 130 | 0 | 0 | 0 | 110 | 0 | 0 | 0 | 90 | 0 | 0 | 0 | 90 | 0 | 0 | 0 |
| 2 | 10 | 130 | 0 | 0 | 0 | 110 | 0 | 0 | 0 | 110 | 0 | 0 | 0 | 120 | 0 | 0 | 0 |

-continued

| 1 Product | 2 | a | b | c | d | a | b | c | d | a | b | c | d | a | b | c | d |
|---|---|---|---|---|---|---|---|---|---|---|---|---|---|---|---|---|---|
| 3 | 10 | 130 | 0 | 0 | 0 | 60 | 8 | 2 | 2(3)* | 100 | 0 | 0 | 0 | 110 | 0 | 0 | 0 |
| 4 | 10 | 80 | 5 | 1 | 1(1)* | | | | | 120 | 0 | 0 | 0 | 120 | 0 | 0 | 0 |
| 5 | 10 | | | | | | | | | 120 | 17 | 3 | 0 | 120 | 0 | 0 | 0 |
| 6 | 10 | | | | | | | | | 80 | 25 | 10 | 3(9)* | 100 | 11 | 8 | 2(4)* |

| 1 Product | 2 | a | b | c | d | a | b | c | d | a | b | c | d | a | b | c | d |
|---|---|---|---|---|---|---|---|---|---|---|---|---|---|---|---|---|---|
| | | | IAM 5 | | | | IAM 6 | | | | IAM 7 | | | | IAM 8 | | |
| 1 | 10 | 130 | 0 | 0 | 0 | 110 | 0 | 0 | 0 | 120 | 0 | 0 | 0 | 100 | 0 | 0 | 0 |
| 2 | 10 | 110 | 0 | 0 | 0 | 110 | 0 | 0 | 0 | 110 | 0 | 0 | 0 | 120 | 0 | 0 | 0 |
| 3 | 10 | 110 | 0 | 0 | 0 | 110 | 0 | 0 | 0 | 120 | 0 | 0 | 0 | 120 | 0 | 0 | 0 |
| 4 | 10 | 110 | 7 | 2 | 0 | 110 | 6 | 2 | 0 | 100 | 6 | 1 | 0 | 110 | 0 | 0 | 0 |
| 5 | 10 | 100 | 12 | 4 | 0 | 110 | 16 | 5 | 0 | 100 | 13 | 4 | 0 | 110 | 0 | 0 | 0 |
| 6 | 10 | 70 | 10 | 3 | 1(2)* | 80 | 20 | 9 | 2(4)* | 80 | 22 | 11 | 3(3)* | 50 | 11 | 8 | 2(1)* |

| 1 Product | 2 | a | b | c | d | a | b | c | d | a | b | c | d | a | b | c | d |
|---|---|---|---|---|---|---|---|---|---|---|---|---|---|---|---|---|---|
| | | | IAM 9 | | | | IAM 10 | | | | IAM 11 | | | | IAM 12 | | |
| 1 | 10 | 100 | 0 | 0 | 0 | 100 | 0 | 0 | 0 | 130 | 0 | 0 | 0 | 130 | 0 | 0 | 0 |
| 2 | 10 | 100 | 0 | 0 | 0 | 100 | 0 | 0 | 0 | 110 | 0 | 0 | 0 | 130 | 0 | 0 | 0 |
| 3 | 10 | 100 | 0 | 0 | 0 | 110 | 0 | 0 | 0 | 100 | 0 | 0 | 0 | 130 | 0 | 0 | 0 |
| 4 | 10 | 100 | 0 | 0 | 0 | 120 | 2 | 0 | 0 | 110 | 4 | 2 | 0 | 120 | 15 | 0 | 0 |
| 5 | 10 | 90 | 9 | 3 | 0 | 100 | 9 | 3 | 0 | 100 | 11 | 5 | 0 | 120 | 15 | 2 | 0 |
| 6 | 10 | 50 | 17 | 7 | 4(1)* | 90 | 18 | 10 | 5(1)* | 80 | 21 | 14 | 4(2)* | 110 | 31 | 8 | 4(2)* |

| 1 Product | 2 | a | b | c | d | a | b | c | d | a | b | c | d | a | b | c | d |
|---|---|---|---|---|---|---|---|---|---|---|---|---|---|---|---|---|---|
| | | | IAM 13 | | | | IAM 14 | | | | IAM 15 | | | | IAM 16 | | |
| 1 | 10 | 130 | 0 | 0 | 0 | 100 | 0 | 0 | 0 | 120 | 0 | 0 | 0 | 80 | 0 | 0 | 0 |
| 2 | 10 | 120 | 0 | 0 | 0 | 100 | 0 | 0 | 0 | 90 | 0 | 0 | 0 | 100 | 0 | 0 | 0 |
| 3 | 10 | 130 | 0 | 0 | 0 | 120 | 0 | 0 | 0 | 90 | 0 | 0 | 0 | 120 | 0 | 0 | 0 |
| 4 | 10 | 120 | 15 | 1 | 0 | 120 | 22 | 5 | 0 | 90 | 4 | 1 | 0 | 110 | 4 | 0 | 0 |
| 5 | 10 | 100 | 16 | 2 | 0 | 110 | 22 | 5 | 0 | 100 | 14 | 8 | 0 | 110 | 30 | 5 | 0 |
| 6 | 10 | 100 | 37 | 17 | 1(1)* | 100 | 28 | 22 | 2(3)* | 100 | 29 | 10 | 3(2)* | 100 | 32 | 18 | 5(4)* |

| 1 Product | 2 | a | b | c | d | a | b | c | d | a | b | c | d | a | b | c | d |
|---|---|---|---|---|---|---|---|---|---|---|---|---|---|---|---|---|---|
| | | | IAM 17 | | | | IAM 18 | | | | IAM 19 | | | | IAM 20 | | |
| 1 | 10 | 80 | 0 | 0 | 0 | 100 | 0 | 0 | 0 | 70 | 0 | 0 | 0 | 130 | 0 | 0 | 0 |
| 2 | 10 | 100 | 0 | 0 | 0 | 130 | 0 | 0 | 0 | 120 | 0 | 0 | 0 | 100 | 0 | 0 | 0 |
| 3 | 10 | 110 | 5 | 0 | 0 | 120 | 4 | 0 | 0 | 120 | 0 | 0 | 0 | 120 | 0 | 0 | 0 |
| 4 | 10 | 120 | 5 | 2 | 0 | 130 | 9 | 6 | 0 | 100 | 10 | 2 | 0 | 130 | 3 | 1 | 0 |
| 5 | 10 | 120 | 19 | 13 | 3(3)* | 110 | 25 | 16 | 4(3)* | 110 | 27 | 13 | 0 | 120 | 12 | 6 | 0 |
| 6 | 10 | | | | | | | | | 40 | 20 | 11 | 4(3)* | 50 | 11 | 8 | 2(4)* |

| 1 Product | 2 | a | b | c | d | a | b | c | d | a | b | c | d | a | b | c | d |
|---|---|---|---|---|---|---|---|---|---|---|---|---|---|---|---|---|---|
| | | | IAM 21 | | | | IAM 22 | | | | IAM 23 | | | | IAM 24 | | |
| 1 | 10 | 80 | 0 | 0 | 0 | 90 | 0 | 0 | 0 | 90 | 0 | 0 | 0 | 130 | 0 | 0 | 0 |
| 2 | 10 | 80 | 0 | 0 | 0 | 100 | 0 | 0 | 0 | 110 | 0 | 0 | 0 | 130 | 0 | 0 | 0 |
| 3 | 10 | 100 | 0 | 0 | 0 | 110 | 0 | 0 | 0 | 100 | 0 | 0 | 0 | 100 | 4 | 0 | 0 |
| 4 | 10 | 100 | 0 | 0 | 0 | 120 | 14 | 6 | 0 | 120 | 0 | 0 | 0 | 100 | 7 | 0 | 0 |
| 5 | 10 | 100 | 29 | 13 | 0 | 100 | 12 | 6 | 0 | 90 | 37 | 9 | 0 | 120 | 12 | 3 | 0 |
| 6 | 10 | 100 | 14 | 1 | 1(1)* | 80 | 21 | 10 | 3(1)* | 40 | 5 | 5 | 3(1)* | 20 | 13 | 2 | 2(1)* |

| 1 Product | 2 | a | b | c | d | a | b | c | d | a | b | c | d | a | b | c | d |
|---|---|---|---|---|---|---|---|---|---|---|---|---|---|---|---|---|---|
| | | | IAM 25 | | | | IAM 26 | | | | IAM 27 | | | | IAM 28 | | |
| 1 | 10 | 130 | 0 | 0 | 0 | 130 | 0 | 0 | 0 | 120 | 0 | 0 | 0 | 100 | 0 | 0 | 0 |
| 2 | 10 | 120 | 0 | 0 | 0 | 120 | 0 | 0 | 0 | 120 | 0 | 0 | 0 | 100 | 0 | 0 | 0 |
| 3 | 10 | 130 | 4 | 1 | 0 | 130 | 0 | 0 | 0 | 100 | 4 | 0 | 0 | 100 | 3 | 0 | 0 |
| 4 | 10 | 110 | 15 | 3 | 0 | 100 | 6 | 3 | 0 | 100 | 7 | 0 | 0 | 100 | 8 | 0 | 0 |
| 5 | 10 | 100 | 12 | 8 | 0 | 100 | 16 | 4 | 0 | 100 | 20 | 7 | 0 | 100 | 17 | 4 | 0 |
| 6 | 10 | 20 | 7 | 7 | 1(1)* | 40 | 5 | 5 | 5(1)* | 30 | 2 | 2 | 2(1)* | 10 | 15 | 5 | 2(1)* |

| 1 Product | 2 | a | b | c | d | a | b | c | d | a | b | c | d | a | b | c | d |
|---|---|---|---|---|---|---|---|---|---|---|---|---|---|---|---|---|---|
| | | | IAM 29 | | | | IAM 30 | | | | IAM 31 | | | | IAM 32 | | |
| 1 | 10 | 140 | 0 | 0 | 0 | 110 | 0 | 0 | 0 | 120 | 0 | 0 | 0 | 130 | 0 | 0 | 0 |
| 2 | 10 | 140 | 0 | 0 | 0 | 110 | 0 | 0 | 0 | 120 | 3 | 0 | 0 | 120 | 0 | 0 | 0 |
| 3 | 10 | 150 | 5 | 0 | 0 | 110 | 3 | 0 | 0 | 120 | 5 | 0 | 0 | 120 | 10 | 0 | 0 |
| 4 | 10 | 100 | 9 | 1 | 0 | 110 | 13 | 4 | 0 | 120 | 9 | 4 | 0 | 120 | 20 | 5 | 0 |
| 5 | 10 | 20 | 12 | 5 | 2(2)* | 10 | 2 | 2 | 2(1)* | 20 | 1 | 1(1)* | 0 | 30 | 6 | 3 | 3(§)* |
| 6 | | | | | | | | | | | | | | | | | | |

| 1 Product | 2 | a | b | c | d | a | b | c | d | a | b | c | d | a | b | c | d |
|---|---|---|---|---|---|---|---|---|---|---|---|---|---|---|---|---|---|
| | | | IAM 33 | | | | IAM 34 | | | | IAM 35 | | | | IAM 36 | | |
| 1 | 10 | 100 | 0 | 0 | 0 | 100 | 0 | 0 | 0 | 110 | 0 | 0 | 0 | 120 | 0 | 0 | 0 |
| 2 | 10 | 100 | 0 | 0 | 0 | 90 | 0 | 0 | 0 | 100 | 0 | 0 | 0 | 100 | 0 | 0 | 0 |

-continued

| 1 Product | 2 | a | b | c | d | a | b | c | d | a | b | c | d | a | b | c | d |
|---|---|---|---|---|---|---|---|---|---|---|---|---|---|---|---|---|---|
| 3 | 10 | 90 | 0 | 0 | 0 | 90 | 0 | 0 | 0 | 100 | 0 | 0 | 0 | 120 | 0 | 0 | 0 |
| 4 | 10 | 90 | 0 | 0 | 0 | 100 | 0 | 0 | 0 | 100 | 0 | 0 | 0 | 100 | 10 | 0 | 0 |
| 5 | 10 | 100 | 4 | 1 | 0 | 100 | 5 | 4 | 0 | 100 | 7 | 3 | 0 | 100 | 30 | 8 | 0 |
| 6 | 10 | 80 | 6 | 6 | 2(4)* | 60 | 8 | 2 | 2(3)* | 60 | 10 | 10 | 3(1)* | 100 | 15 | 10 | 4(2)* |

| 1 Product | 2 | a | b | c | d | a | b | c | d | a | b | c | d | a | b | c | d |
|---|---|---|---|---|---|---|---|---|---|---|---|---|---|---|---|---|---|
|  |  | IAM 37 | | | | IAM 38 | | | | IAM 39 | | | | IAM 40 | | | |
| 1 | 10 | 70 | 0 | 0 | 0 | 120 | 0 | 0 | 0 | 90 | 0 | 0 | 0 | 110 | 0 | 0 | 0 |
| 2 | 10 | 70 | 0 | 0 | 0 | 120 | 0 | 0 | 0 | 90 | 0 | 0 | 0 | 90 | 0 | 0 | 0 |
| 3 | 10 | 100 | 0 | 0 | 0 | 100 | 0 | 0 | 0 | 90 | 0 | 0 | 0 | 90 | 2 | 0 | 0 |
| 4 | 10 | 110 | 10 | 1 | 0 | 90 | 11 | 3 | 0 | 100 | 6 | 1 | 0 | 100 | 12 | 3 | 0 |
| 5 | 10 | 110 | 19 | 8 | 0 | 90 | 15 | 6 | 0 | 100 | 17 | 6 | 0 | 110 | 20 | 6 | 0 |
| 6 | 10 | 100 | 17 | 7 | 3(7)* | 70 | 18 | 5 | 3(6)* | 100 | 5 | 5 | 3(2)* | 110 | 3 | 3 | 3(1)* |

| 1 Product | 2 | a | b | c | d | a | b | c | d | a | b | c | d | a | b | c | d |
|---|---|---|---|---|---|---|---|---|---|---|---|---|---|---|---|---|---|
|  |  | IAM 41 | | | | IAM 42 | | | | IAM 43 | | | | IAM 44 | | | |
| 1 | 10 | 100 | 0 | 0 | 0 | 80 | 0 | 0 | 0 | 100 | 0 | 0 | 0 | 120 | 0 | 0 | 0 |
| 2 | 10 | 110 | 0 | 0 | 0 | 120 | 0 | 0 | 0 | 110 | 0 | 0 | 0 | 120 | 0 | 0 | 0 |
| 3 | 10 | 120 | 3 | 0 | 0 | 130 | 7 | 0 | 0 | 110 | 0 | 0 | 0 | 120 | 0 | 0 | 0 |
| 4 | 10 | 110 | 15 | 4 | 0 | 130 | 18 | 4 | 0 | 100 | 0 | 0 | 0 | 120 | 0 | 0 | 0 |
| 5 | 10 | 110 | 19 | 7 | 0 | 120 | 25 | 10 | 0 | 100 | 1 | 0 | 0 | 90 | 0 | 0 | 0 |
| 6 | 10 | 60 | 7 | 7 | 1(1)* | 50 | 2 | 2 | 2(1)* | 110 | 7 | 1 | 0 | 90 | 3 | 1 | 0 |
| 7 | 10 |  |  |  |  |  |  |  |  | 70 | 18 | 6 | 3(4)* | 100 | 21 | 8 | 3(2)* |

| 1 Product | 2 | a | b | c | d | a | b | c | d | a | b | c | d | a | b | c | d |
|---|---|---|---|---|---|---|---|---|---|---|---|---|---|---|---|---|---|
|  |  | IAM 45 | | | | IAM 46 | | | | IAM 47 | | | | IAM 48 | | | |
| 1 | 10 | 130 | 0 | 0 | 0 | 80 | 0 | 0 | 0 | 90 | 0 | 0 | 0 | 100 | 0 | 0 | 0 |
| 2 | 10 | 120 | 0 | 0 | 0 | 120 | 0 | 0 | 0 | 110 | 0 | 0 | 0 | 90 | 0 | 0 | 0 |
| 3 | 10 | 120 | 0 | 0 | 0 | 130 | 0 | 0 | 0 | 110 | 0 | 0 | 0 | 100 | 0 | 0 | 0 |
| 4 | 10 | 120 | 5 | 0 | 0 | 130 | 8 | 4 | 0 | 90 | 0 | 0 | 0 | 90 | 0 | 0 | 0 |
| 5 | 10 | 100 | 9 | 4 | 0 | 120 | 15 | 10 | 0 | 100 | 1 | 0 | 0 | 90 | 0 | 0 | 0 |
| 6 | 10 | 110 | 35 | 9 | 0 | 100 | 22 | 12 | 0 | 100 | 7 | 1 | 0 | 90 | 3 | 1 | 0 |
| 7 | 10 | 30 | 21 | 14 | 4(1)* | 50 | 12 | 12 | 2(1)* | 70 | 15 | 5 | 3(6)* | 90 | 6 | 3 | 0 |
| 8 | 10 |  |  |  |  |  |  |  |  |  |  |  |  | 50 | 14 | 10 | 5(2)* |

| 1 Product | 2 | a | b | c | d | a | b | c | d | a | b | c | d | a | b | c | d |
|---|---|---|---|---|---|---|---|---|---|---|---|---|---|---|---|---|---|
|  |  | IAM 49 | | | | IAM 50 | | | | IAM 51 | | | | IAM 52 | | | |
| 1 | 10 | 80 | 0 | 0 | 0 | 100 | 0 | 0 | 0 | 130 | 0 | 0 | 0 | 100 | 0 | 0 | 0 |
| 2 | 10 | 80 | 0 | 0 | 0 | 120 | 0 | 0 | 0 | 130 | 0 | 0 | 0 | 90 | 0 | 0 | 0 |
| 3 | 10 | 120 | 0 | 0 | 0 | 110 | 0 | 0 | 0 | 110 | 0 | 0 | 0 | 100 | 0 | 0 | 0 |
| 4 | 10 | 120 | 0 | 0 | 0 | 110 | 0 | 0 | 0 | 120 | 0 | 0 | 0 | 90 | 0 | 0 | 0 |
| 5 | 10 | 120 | 0 | 0 | 0 | 110 | 0 | 0 | 0 | 120 | 1 | 0 | 0 | 90 | 0 | 0 | 0 |
| 6 | 10 | 120 | 5 | 3 | 0 | 110 | 2 | 1 | 0 | 110 | 7 | 1 | 0 | 90 | 3 | 1 | 0 |
| 7 | 10 | 130 | 11 | 4 | 0 | 110 | 18 | 12 | 0 | 120 | 18 | 6 | 0 | 90 | 6 | 3 | 0 |
| 8 | 10 | 60 | 8 | 4 | 4(2)* | 80 | 10 | 8 | 2(1)* | 80 | 12 | 9 | 5(2)* | 50 | 15 | 8 | 3(3)* |

| 1 Product | 2 | a | b | c | d | a | b | c | d | a | b | c | d | a | b | c | d |
|---|---|---|---|---|---|---|---|---|---|---|---|---|---|---|---|---|---|
|  |  | IAM 53 | | | | IAM 54 | | | | IAM 55 | | | | IAM 56 | | | |
| 1 | 10 | 90 | 0 | 0 | 0 | 70 | 0 | 0 | 0 | 80 | 0 | 0 | 0 | 100 | 0 | 0 | 0 |
| 2 | 10 | 100 | 0 | 0 | 0 | 90 | 0 | 0 | 0 | 100 | 0 | 0 | 0 | 100 | 0 | 0 | 0 |
| 3 | 10 | 110 | 0 | 0 | 0 | 110 | 0 | 0 | 0 | 100 | 0 | 0 | 0 | 100 | 0 | 0 | 0 |
| 4 | 10 | 120 | 0 | 0 | 0 | 120 | 0 | 0 | 0 | 100 | 0 | 0 | 0 | 100 | 0 | 0 | 0 |
| 5 | 10 | 110 | 5 | 0 | 0 | 100 | 0 | 0 | 0 | 90 | 0 | 0 | 0 | 110 | 0 | 0 | 0 |
| 6 | 10 | 100 | 8 | 2 | 0 | 90 | 0 | 0 | 0 | 110 | 0 | 0 | 0 | 110 | 0 | 0 | 0 |
| 7 | 10 | 100 | 17 | 8 | 0 | 90 | 5 | 2 | 0 | 100 | 8 | 4 | 0 | 100 | 6 | 1 | 0 |
| 8 | 10 | 40 | 11 | 10 | 2(3)* | 100 | 14 | 3 | 0 | 100 | 15 | 3 | 0 | 100 | 18 | 10 |  |
| 9 | 10 |  |  |  |  | 50 | 16 | 8 | 2(1)* | 50 | 4 | 4 | 1(2)* | 70 | 5 | 5 | 5(1)* |

| 1 Product | 2 | a | b | c | d | a | b | c | d | a | b | c | d | a | b | c | d |
|---|---|---|---|---|---|---|---|---|---|---|---|---|---|---|---|---|---|
|  |  | IAM 57 | | | | IAM 58 | | | | IAM 59 | | | | IAM 60 | | | |
| 1 | 10 | 60 | 0 | 0 | 0 | 90 | 0 | 0 | 0 | 70 | 0 | 0 | 0 | 50 | 0 | 0 | 0 |
| 2 | 10 | 60 | 0 | 0 | 0 | 90 | 0 | 0 | 0 | 90 | 0 | 0 | 0 | 90 | 0 | 0 | 0 |
| 3 | 10 | 100 | 0 | 0 | 0 | 100 | 0 | 0 | 0 | 80 | 0 | 0 | 0 | 100 | 0 | 0 | 0 |
| 4 | 10 | 130 | 0 | 0 | 0 | 100 | 0 | 0 | 0 | 120 | 0 | 0 | 0 | 130 | 0 | 0 | 0 |
| 5 | 10 | 100 | 0 | 0 | 0 | 110 | 0 | 0 | 0 | 120 | 0 | 0 | 0 | 120 | 0 | 0 | 0 |
| 6 | 10 | 110 | 6 | 0 | 0 | 100 | 10 | 0 | 0 | 130 | 0 | 0 | 0 | 120 | 0 | 0 | 0 |
| 7 | 10 | 110 | 23 | 2 | 0 | 110 | 10 | 1 | 0 | 130 | 24 | 0 | 0 | 120 | 17 | 0 | 0 |
| 8 | 10 | 100 | 14 | 5 | 0 | 110 | 24 | 5 | 0 | 130 | 30 | 0 | 0 | 100 | 28 | 0 | 0 |
| 9 | 10 | 90 | 9 | 4 | 2(4)* | 80 | 6 | 6 | 3(1)* | 100 | 14 | 5 | 1(7)* | 80 | 36 | 4 | 2(3)* |

-continued

| 1 | 2 | a | b | c | d | a | b | c | d | a | b | c | d | a | b | c | d |
|---|---|---|---|---|---|---|---|---|---|---|---|---|---|---|---|---|---|
| Product | | IAM 61 | | | | IAM 62 | | | | IAM 63 | | | | IAM 64 | | | |
| 1 | 10 | 90  | 0  | 0  | 0 | 100 | 0  | 0  | 0 | 110 | 0  | 0  | 0 | 100 | 0  | 0  | 0 |
| 2 | 10 | 100 | 0  | 0  | 0 | 90  | 0  | 0  | 0 | 90  | 0  | 0  | 0 | 100 | 0  | 0  | 0 |
| 3 | 10 | 110 | 0  | 0  | 0 | 110 | 0  | 0  | 0 | 130 | 0  | 0  | 0 | 110 | 0  | 0  | 0 |
| 4 | 10 | 120 | 0  | 0  | 0 | 120 | 0  | 0  | 0 | 120 | 0  | 0  | 0 | 100 | 0  | 0  | 0 |
| 5 | 10 | 110 | 10 | 0  | 0 | 100 | 10 | 0  | 0 | 110 | 6  | 0  | 0 | 110 | 0  | 0  | 0 |
| 6 | 10 | 100 | 12 | 0  | 0 | 90  | 10 | 0  | 0 | 130 | 14 | 0  | 0 | 110 | 0  | 0  | 0 |
| 7 | 10 | 100 | 20 | 8  | 0 | 100 | 15 | 1  | 0 | 120 | 28 | 0  | 0 | 100 | 6  | 1  | 0 |
| 8 | 10 | 120 | 35 | 6  | 0 | 100 | 44 | 10 | 0 | 100 | 35 | 3  | 0 | 100 | 18 | 10 | 0 |
| 9 | 10 | 100 | 10 | 10 | 2(1)* | 50 | 50 | 20 | 9(1)* | 20 | 10 | 10 | 7(1)* | 70 | 5 | 5 | 5(1)* |

| 1 | 2 | a | b | c | d | a | b | c | d | a | b | c | d | a | b | c | d |
|---|---|---|---|---|---|---|---|---|---|---|---|---|---|---|---|---|---|
| Product | | IAM 65 | | | | IAM 66 | | | | IAM 67 | | | | IAM 68 | | | |
| 1 | 10 | 120 | 0  | 0  | 0 | 100 | 0  | 0  | 0 | 100 | 0  | 0  | 0 | 80  | 0  | 0  | 0 |
| 2 | 10 | 120 | 0  | 0  | 0 | 110 | 0  | 0  | 0 | 100 | 0  | 0  | 0 | 80  | 0  | 0  | 0 |
| 3 | 10 | 120 | 0  | 0  | 0 | 120 | 0  | 0  | 0 | 120 | 0  | 0  | 0 | 90  | 0  | 0  | 0 |
| 4 | 10 | 100 | 0  | 0  | 0 | 130 | 0  | 0  | 0 | 130 | 0  | 0  | 0 | 140 | 0  | 0  | 0 |
| 5 | 10 | 100 | 12 | 0  | 0 | 140 | 10 | 0  | 0 | 110 | 0  | 0  | 0 | 120 | 6  | 0  | 0 |
| 6 | 10 | 100 | 28 | 0  | 0 | 110 | 20 | 0  | 0 | 120 | 23 | 0  | 0 | 90  | 12 | 0  | 0 |
| 7 | 10 | 90  | 37 | 2  | 0 | 110 | 25 | 4  | 0 | 120 | 23 | 0  | 0 | 90  | 17 | 3  | 0 |
| 8 | 10 | 110 | 41 | 15 | 0 | 120 | 34 | 10 | 0 | 120 | 21 | 7  | 0 | 110 | 15 | 3  | 0 |
| 9 | 10 | 30  | 11 | 11 | 8(1)* | 30 | 12 | 10 | 4(1)* | 40 | 14 | 11 | 4(1)* | 70 | 24 | 14 | 5(4)* |

| 1 | 2 | a | b | c | d | a | b | c | d | a | b | c | d | a | b | c | d |
|---|---|---|---|---|---|---|---|---|---|---|---|---|---|---|---|---|---|
| Product | | IAM 69 | | | | IAM 70 | | | | IAM 71 | | | | IAM 72 | | | |
| 1  | 10 | 70  | 0  | 0  | 0 | 80  | 0  | 0  | 0 | 120 | 0  | 0  | 0 | 100 | 0  | 0  | 0 |
| 2  | 10 | 100 | 0  | 0  | 0 | 80  | 0  | 0  | 0 | 110 | 0  | 0  | 0 | 120 | 0  | 0  | 0 |
| 3  | 10 | 100 | 0  | 0  | 0 | 100 | 0  | 0  | 0 | 100 | 0  | 0  | 0 | 100 | 0  | 0  | 0 |
| 4  | 10 | 110 | 0  | 0  | 0 | 100 | 0  | 0  | 0 | 100 | 0  | 0  | 0 | 110 | 5  | 0  | 0 |
| 5  | 10 | 120 | 2  | 0  | 0 | 90  | 1  | 1  | 0 | 90  | 6  | 0  | 0 | 120 | 10 | 2  | 0 |
| 6  | 10 | 110 | 8  | 2  | 0 | 100 | 10 | 3  | 0 | 80  | 13 | 1  | 0 | 100 | 14 | 3  | 0 |
| 7  | 10 | 100 | 7  | 2  | 0 | 90  | 22 | 6  | 0 | 120 | 21 | 4  | 0 | 110 | 20 | 5  | 0 |
| 8  | 10 | 80  | 11 | 1  | 0 | 100 | 30 | 14 | 0 | 100 | 25 | 8  | 0 | 90  | 20 | 8  | 0 |
| 9  | 10 | 100 | 14 | 12 | 0 | 20  | 13 | 11 | 5(1)* | 30 | 34 | 13 | 3(1)* | 40 | 8 | 8 | 2(1)* |
| 10 | 10 | 10  | 10 | 10 | 3(1)* | | | | | | | | | | | | |

| 1 | 2 | a | b | c | d | a | b | c | d | a | b | c | d | a | b | c | d |
|---|---|---|---|---|---|---|---|---|---|---|---|---|---|---|---|---|---|
| Product | | IAM 73 | | | | IAM 74 | | | | IAM 75 | | | | IAM 76 | | | |
| 1  | 10 | 120 | 0  | 0  | 0 | 80  | 0  | 0  | 0 | 90   | 0  | 0  | 0 | 110 | 0  | 0  | 0 |
| 2  | 10 | 120 | 0  | 0  | 0 | 80  | 0  | 0  | 0 | 90   | 0  | 0  | 0 | 110 | 0  | 0  | 0 |
| 3  | 10 | 120 | 0  | 0  | 0 | 100 | 0  | 0  | 0 | 120  | 0  | 0  | 0 | 120 | 0  | 0  | 0 |
| 4  | 10 | 100 | 0  | 0  | 0 | 100 | 0  | 0  | 0 | 110  | 4  | 0  | 0 | 130 | 0  | 0  | 0 |
| 5  | 10 | 100 | 0  | 0  | 0 | 90  | 0  | 0  | 0 | 70   | 12 | 2  | 0 | 100 | 20 | 4  | 0 |
| 6  | 10 | 130 | 22 | 0  | 0 | 100 | 7  | 0  | 0 | 90   | 20 | 3  | 0 | 110 | 23 | 4  | 0 |
| 7  | 10 | 90  | 35 | 3  | 0 | 90  | 16 | 1  | 0 | 130  | 34 | 6  | 0 | 90  | 17 | 3  | 0 |
| 8  | 10 | 90  | 33 | 3  | 0 | 100 | 30 | 1  | 0 | 1010 | 35 | 5  | 0 | 70  | 15 | 7  | 0 |
| 9  | 10 | 30  | 10 | 10 | 4(2)* | 20 | 33 | 1 | 0 | 20 | 44 | 3 | 3(1)* | 20 | 4 | 4 | 4(1)* |
| 10 | 10 | | | | | 20 | 8 | 7 | 3(1)* | | | | | | | | |

| 1 | 2 | a | b | c | d | a | b | c | d | a | b | c | d | a | b | c | d |
|---|---|---|---|---|---|---|---|---|---|---|---|---|---|---|---|---|---|
| Product | | IAM 77 | | | | IAM 78 | | | | IAM 79 | | | | IAM 80 | | | |
| 1  | 10 | 100 | 0  | 0  | 0 | 70  | 0  | 0  | 0 | 120 | 0  | 0  | 0 | 60  | 0  | 0  | 0 |
| 2  | 10 | 90  | 0  | 0  | 0 | 90  | 0  | 0  | 0 | 110 | 0  | 0  | 0 | 90  | 0  | 0  | 0 |
| 3  | 10 | 100 | 0  | 0  | 0 | 90  | 0  | 0  | 0 | 100 | 0  | 0  | 0 | 100 | 0  | 0  | 0 |
| 4  | 10 | 100 | 0  | 0  | 0 | 110 | 4  | 0  | 0 | 100 | 0  | 0  | 0 | 130 | 0  | 0  | 0 |
| 5  | 10 | 100 | 15 | 2  | 0 | 90  | 13 | 2  | 0 | 90  | 6  | 0  | 0 | 100 | 20 | 0  | 0 |
| 6  | 10 | 100 | 20 | 5  | 0 | 120 | 12 | 4  | 0 | 80  | 13 | 1  | 0 | 110 | 20 | 6  | 0 |
| 7  | 10 | 100 | 20 | 1  | 0 | 120 | 26 | 3  | 0 | 120 | 21 | 4  | 0 | 120 | 35 | 3  | 0 |
| 8  | 10 | 100 | 30 | 10 | 0 | 110 | 33 | 9  | 0 | 100 | 25 | 8  | 0 | 100 | 30 | 5  | 0 |
| 9  | 10 | 30  | 7  | 6  | 2(1)* | 50 | 5 | 5 | 5(1)* | 30 | 34 | 13 | 3(1)* | 50 | 12 | 12 | 6(3)* |
| 10 | 10 | | | | | | | | | 10 | 10 | 10 | 3(1)* | | | | |

| 1 | 2 | a | b | c | d | a | b | c | d | a | b | c | d | a | b | c | d |
|---|---|---|---|---|---|---|---|---|---|---|---|---|---|---|---|---|---|
| Product | | IAM 81 | | | | IAM 82 | | | | IAM 83 | | | | IAM 84 | | | |
| 1 | 10 | 100 | 0  | 0 | 0 | 100 | 0  | 0 | 0 | 70  | 0  | 0 | 0 | 60  | 0  | 0 | 0 |
| 2 | 10 | 100 | 0  | 0 | 0 | 80  | 0  | 0 | 0 | 100 | 0  | 0 | 0 | 80  | 0  | 0 | 0 |
| 3 | 10 | 100 | 0  | 0 | 0 | 100 | 0  | 0 | 0 | 120 | 0  | 0 | 0 | 70  | 0  | 0 | 0 |
| 4 | 10 | 110 | 0  | 0 | 0 | 90  | 0  | 0 | 0 | 100 | 0  | 0 | 0 | 100 | 0  | 0 | 0 |
| 5 | 10 | 120 | 0  | 0 | 0 | 90  | 8  | 0 | 0 | 100 | 10 | 0 | 0 | 100 | 0  | 0 | 0 |
| 6 | 10 | 110 | 28 | 2 | 0 | 110 | 19 | 2 | 0 | 110 | 20 | 2 | 0 | 90  | 4  | 0 | 0 |
| 7 | 10 | 100 | 27 | 2 | 0 | 100 | 25 | 2 | 0 | 90  | 25 | 6 | 0 | 120 | 25 | 0 | 0 |
| 8 | 10 | 100 | 30 | 1 | 0 | 110 | 36 | 7 | 0 | 190 | 25 | 5 | 0 | 100 | 25 | 2 | 0 |

-continued

| 9 | 10 | 20 | 30 | 18 | 8(1)* | 20 | 9 | 9 | 3(1)* | 40 | 15 | 13 | 6(1)* | 100 | 25 | 2 | 0 |
| 10 | 10 | | | | | | | | | | | | | 40 | 22 | 5 | 3(3)* |

| 1 | 2 | a | b | c | d | a | b | c | d |
|---|---|---|---|---|---|---|---|---|---|
| Poduct | | | IAM 85 | | | | IAM 86 | | |
| 1 | 10 | 70 | 0 | 0 | 0 | 70 | 0 | 0 | 0 |
| 2 | 10 | 70 | 0 | 0 | 0 | 80 | 0 | 0 | 0 |
| 3 | 10 | 80 | 0 | 0 | 0 | 90 | 0 | 0 | 0 |
| 4 | 10 | 100 | 5 | 0 | 0 | 130 | 0 | 0 | 0 |
| 5 | 10 | 120 | 10 | 1 | 0 | 130 | 0 | 0 | 0 |
| 6 | 10 | 120 | 20 | 0 | 0 | 120 | 15 | 2 | 0 |
| 7 | 10 | 110 | 25 | 0 | 0 | 110 | 15 | 6 | 0 |
| 8 | 10 | 80 | 37 | 5 | 0 | 100 | 30 | 4 | 0 |
| 9 | 10 | 20 | 9 | 9 | 4(2)* | 40 | 9 | 8 | 2(1)* |

2. Series of Tests for Repellence Against Ticks on Guinea Pigs

On a total of twelve adult, female guinea pigs the right side was shaved to an extent of about 4×4 cm and the skin and surrounding hairy locations were treated manually with in each case approx. 2 ml of the respective test product, covering the full surface. Then each hour, one adult tick in each case of the genus common tick (*Ixodes ricinus*), raised in the laboratory and kept hungry for two weeks, was placed in the centre of the treated, shaved area using tweezers and its behaviour was observed. The guinea pigs were not sedated as is usual, but instead, to simulate as natural a situation as possible, were fed with lettuce and they remained rather calm, because they are used to a human environment.

It was immediately noticeable that the ticks did not, as on the untreated guinea pig serving as the control animal (CA), start to wander around looking for a suitable place to bite into (normally a bending fold under the rear legs), but rather moved over the treated surface in a tight circle for a few minutes and then, with the slightest movement from their hosts, fell to the bottom of the cage, although ticks normally can find a hold with their holding claws on even smooth surfaces. The fallen ticks were immediately placed in labelled jars and observed over 72 hours. After this time period all observed ticks were dead.

List of Test Individuals and Test Products:
 the untreated controls were labelled with CA;
 the experimental animal treated with the reference product ANTI BRUMM with REF; and
 the experimental animals treated with the compositions according to the invention were labelled with IAM 1, IAM 4, IAM 38, IAM 43, IAM 48, IAM 54, IAM 59, IAM 64, IAM 74 and IAM 84.

Results of Effectiveness:
CA: after a short orientation phase, each of the ticks placed in location hourly and individually within the test time over 8 hours, soon began to bore and suck blood, whereupon they were immediately removed so as not to weaken the control animal.

REF: the ticks during the first 2 hours fell down as with the products of the IAM series and were dead within 72 hours. The tick applied in the $3^{rd}$ hour began to bore down, whereupon the test was interrupted and the protection time was therefore 2 hours.

Protection Times for the Compositions According to the Invention Against Ticks on Guinea Pigs:
X=Protection time
Y=Time of the first boring down of a freshly applied tick

| Product | IAM 1 | IAM 4 | IAM 38 | IAM 43 | IAM 48 | IAM 54 | IAM 59 | IAM 64 | IAM 74 | IAM 84 |
|---|---|---|---|---|---|---|---|---|---|---|
| 1 hr. | | | | | | | | | | |
| 2 hrs. | | | | | | | | | | |
| 3 hrs. | x | | | | | | | | | |
| 4 hrs. | y | | x | | x | | | | | |
| 5 hrs. | | y | | | y | x | x | | x | |
| 6 hrs. | | | | x | | y | y | x | y | |
| 7 hrs. | | x | | y | | | | y | | x |
| 8 hrs. | | y | | | | | | | | y |

All ticks which fell off without attempting to bore down were dead within the observation period of 72 hours.

3. Series of Tests for Repellence Against Ticks on the Dog

To check the repellent effect against ticks as a typical member of the Acarina and which also represent the most dangerous and widespread member of this genus for people and animals, a five-day free ranging test was carried out. These experiments were not carried out on people for ethical reasons.

Six dogs from an animal home and of mixed breed and sex, but of approximately the same weight were made available together with two dog handlers from the group of personnel, who each over the five days took three of the dogs for a walk each day for 4 hours in a known tick infested region (Föhrenwald on the outskirts of the Vienna new town). Daily in always the same way, the two dogs labelled V1 and V2 were treated with IAM 64, with 10 ml being worked into the dog's coat in each case using a brush. The two dogs labelled V3 and V4 were treated as described above with IAM 79, the dog REF with Kik aktiv and the dog K (control) always remained untreated. The two dog handlers were treated daily on the complete naked body with 10 ml of IAM 84 before they went out, because although they were inoculated against spring-summer encephalitis, the risk of transmission of Lyme disease by tick bites was to be avoided and at the same time the protection time of eight hours against tick bites previously found in the laboratory on shaven guinea pig skin was to be confirmed over 4 hours on humans who were potentially at risk.

As an additional measure for reducing the risk, shoes, socks, long trousers and the dog handlers' jackets, which were closed around the arms and legs by pull cords were sprayed daily with in each case 5 ml of IAM 84 giving full coverage. After each of the daily four-hour walks, the animals and their handlers were examined meticulously for ticks which were documented and collected in labelled jars and observed for any fatalities over 72 hours.

Results of Effectiveness:

a) Handler 1, Dog K and Dogs V1 and V2 Over the five days no ticks were found on the skin of Handler 1 and from the clothing a total of four 4 ticks were removed, which in contrast to Dog K had not worked their way through to the skin, but which already proved to be immobile on removal from the clothing and which did not recuperate over the observation period of 72 hours, whereby the fatal effect of IAM 84 on ticks already noticed in the laboratory test was confirmed.

A total of 66 ticks were removed from the untreated control dog (K) over the five days with all ticks surviving the following observation period, whereby it was established that ticks were present and able to live in the region. No ticks were found on V1 and V2.

b) Handler 2, Dog REF and Dogs V3 and V4

No ticks were found on the clothing or skin of Handler 2 and also V3 and V4 were free of ticks, whereas on the coat of REF over the five days a total of 23 ticks were found which survived the following observation time of 72 hours also without any problem, because they were then removed from the jars and placed on the shaved side of a guinea pig in the laboratory where they immediately looked for a suitable location to bite and immediately on reaching the hair covering they started to bore down, whereupon they were removed with tweezers dipped for five minutes in REF according to the rules of the immersion test of the ectoparasite screening and after 72 hours of a further observation period were again applied to the guinea pig where they again started to bore down.

The result showed that although REF had an acceptable repellence to ticks, it exhibited no fatal effect. The 66 ticks removed from the untreated Dog K were dipped for five minutes in IAM 79 and were dead within thirty minutes (they also did not revive 72 hours later).

4. Use with Insects

A. Reference Products Used (REF)

(I)
0.20% wt. methomyl (carbamate)
99.80% wt. water (II)
0.50% wt. chlorpyriphos
0.37% wt. neopynamin
1.95% wt. methoxychlor
97.18% wt. water (III)
20.00% wt. deltamethrin
10.00% wt. water
0.20% wt. carbopol
69.80% wt. 1,2,3-propantriol B. IAM 86 and IAM 90 were used comparatively in equal quantities to REF (I) and (II) in the laboratory experiment as spray agents for use against the following pests (adults and metamorphoses):

A) *Musca domestica*—Common House Fly
B) *Blatella germanica*—German Cockroach
C) *Lasius niger*—Black Garden Ant
D) *Ixodes ricinus*—Common Tick
E) *Tineola bisselliella*—Common Clothes Moth For the tests 30 samples each of the flying pests A) and E) were put into a cage covered with gauze with a size of 1×1×1 m and each was sprayed with 1 ml of IAM 86 and IAM 90 and REF (I) and REF (II). The animals incapable of flight and lying on the bottom were evaluated after respectively 1, 5, 10 and 20 minutes, as was the mortality or revival rate (recuperation) after 24 hours.

|  | Flies | | | | | Moths | | | | |
| --- | --- | --- | --- | --- | --- | --- | --- | --- | --- | --- |
|  | 1 | 5 | 10 | 20 min. | 24 hrs. | 1 | 5 | 10 | 20 min. | 24 hrs. |
| IAM 86 | 100 | 100 | 100 | 100 | 100 | 100 | 100 | 100 | 100 | 100 |
| IAM 90 | 100 | 100 | 100 | 100 | 100 | 100 | 100 | 100 | 100 | 100 |
| REF (I) | 20 | 80 | 100 | 100 | 95 | 100 | 100 | 100 | 100 | 100 |
| REF (II) | 10 | 70 | 100 | 100 | 100 | 100 | 100 | 100 | 100 | 100 |

Of the creeping pests B), C) and D) 30 samples in each case of mixed metamorphoses were placed in a bath of size 1×1×1 m and sprayed with 1 ml of IAM 86 and REF (1).

|  | IAM 86 | | | | | REF (I) | | | | |
| --- | --- | --- | --- | --- | --- | --- | --- | --- | --- | --- |
|  | 1 | 5 | 10 | 20 min. | 24 hrs. | 1 | 5 | 10 | 20 min. | 24 hrs. |
| Cockroaches | 100 | 100 | 100 | 100 | 100 | 90 | 90 | 100 | 100 | 100 |
| Ants | 100 | 100 | 100 | 100 | 100 | 90 | 90 | 90 | 100 | 100 |
| Ticks | 40 | 60 | 100 | 100 | 100 | 0 | 0 | 20 | 40 | 100 |

The evaluation after the respective expired time acquired exclusively animals lying on their backs which showed no leg or antenna movement under the magnifying glass. Also those experimental setups showed that with the use of the insect repellent according to the invention surprisingly not only a comparable, unexpected effect could be achieved, but rather an effect could be achieved which was even better than with the normal marketed comparative product (REF I).

Long-Term Test

The effectiveness of a permanent coating against cockroaches was assessed in a long-term test over six months. A flat stainless-steel bath with dimensions L=50 cm, W=30 cm, H=2 cm was coated in each case with 2 ml of IAM 1 and 2 ml of REF (III) around the 2 cm high side surfaces and on the bottom and placed in each case in large acrylic glass baths (1×1×1 m). Then the following were placed in the treated stainless steel baths:

Once per month for a total of six consecutive months in each case ten mixed examples (adults and nymphs) of
*Blatella germanica*—German Cockroach
*Periplaneta americana*—American Cockroach and
*Blatta orientalis*—Oriental Cockroach
whereby these were then transferred after product contact into the untreated acrylic baths. Then the treated bath was removed and kept for the other experiments. The contaminated cockroaches were supplied with water and food in the untreated bath and observed. After respectively 5, 10, 30 minutes and 24 hours, the animals lying on their backs were counted and after a further 24 hours observation period the mortality rate as a percentage of the total number of cockroaches used was determined.

*Blatella germanica*

|  | IAM 1 | | | | | REF III | | | | |
|---|---|---|---|---|---|---|---|---|---|---|
|  | Minutes | | | Hours | | Minutes | | | Hours | |
|  | 5 | 10 | 30 | 24 | 48 | 5 | 10 | 30 | 24 | 48 |
| Month 1 | 100 | 100 | 100 | 100 | 100 | 100 | 100 | 100 | 100 | 100 |
| Month 2 | 100 | 100 | 100 | 100 | 100 | 100 | 100 | 100 | 100 | 100 |
| Month 3 | 100 | 100 | 100 | 100 | 100 | 100 | 100 | 100 | 100 | 100 |
| Month 4 | 100 | 100 | 100 | 100 | 100 | 100 | 100 | 100 | 100 | 100 |
| Month 5 | 90 | 90 | 90 | 100 | 100 | 90 | 90 | 90 | 90 | 100 |
| Month 6 | 60 | 70 | 85 | 100 | 100 | 60 | 70 | 70 | 100 | 100 |

*Periplaneta americana*

|  | IAM 1 | | | | | REF III | | | | |
|---|---|---|---|---|---|---|---|---|---|---|
|  | Minutes | | | Hours | | Minutes | | | Hours | |
|  | 5 | 10 | 30 | 24 | 48 | 5 | 10 | 30 | 24 | 48 |
| Month 1 | 100 | 100 | 100 | 100 | 100 | 100 | 100 | 100 | 100 | 100 |
| Month 2 | 100 | 100 | 100 | 100 | 100 | 100 | 100 | 100 | 100 | 100 |
| Month 3 | 100 | 100 | 100 | 100 | 100 | 100 | 100 | 100 | 100 | 100 |
| Month 4 | 100 | 100 | 100 | 100 | 100 | 100 | 100 | 100 | 100 | 100 |
| Month 5 | 80 | 90 | 100 | 100 | 100 | 80 | 100 | 100 | 100 | 100 |
| Month 6 | 50 | 60 | 90 | 100 | 100 | 60 | 60 | 60 | 100 | 100 |

*Blatta orientalis*

|  | IAM 1 | | | | | REF III | | | | |
|---|---|---|---|---|---|---|---|---|---|---|
|  | Minutes | | | Hours | | Minutes | | | Hours | |
|  | 5 | 10 | 30 | 24 | 48 | 5 | 10 | 30 | 24 | 48 |
| Month 1 | 100 | 100 | 100 | 100 | 100 | 100 | 100 | 100 | 100 | 100 |
| Month 2 | 100 | 100 | 100 | 100 | 100 | 90 | 100 | 100 | 100 | 100 |
| Month 3 | 100 | 100 | 100 | 100 | 100 | 85 | 100 | 100 | 100 | 100 |
| Month 4 | 100 | 100 | 100 | 100 | 100 | 60 | 80 | 100 | 100 | 100 |
| Month 5 | 90 | 90 | 90 | 100 | 100 | 0 | 35 | 60 | 90 | 100 |
| Month 6 | 60 | 70 | 85 | 100 | 100 | 0 | 30 | 60 | 85 | 100 |

This long-term experiment shows the surprisingly good and long-lasting effect of the insect repellent used according to the invention, in particular in its 100% effectiveness with mixed species and stages of cockroaches (Blattodea), also after a storage time of six months.

5. Use on Vegetable Plants and Flowers in Nurseries

Test AI:

IAM 91 and IAM 92 were compared with REF (I) and REF (II). To do this, in each case 20 begonias, severely infested with red mites (*Panonychus ulmi*), were completely wetted with a quantity of 20 ml in each case (1 ml per plant) of the respective products.

Results:

With IAM 91 and with IAM 92 as well as with the application of REF (II) all plants were completely free of any infestation at the bonitures after 1, 4, 7 and 14 days. With REF(I) the bonitures were free of infestation only after one day. After 4 days 10% of the initial infestation was counted, after 7 days 50% and after 14 days 100%.

The evaluation of the phytotoxicity of the products after the application (leaf-edge discoloration, necrosis, etc.) after 14 days showed that with IAM 91 and IAM 92 the value 0 was found on the 5-division scale (no visible changes), with REF (1) and REF (II) the value 1 (slight discoloration of the leaves and blooms).

Thus it was shown that the combinations according to the invention had the same effect as the market products REF (I) and REF (II), however without their risks to the health of the users and plants.

Test AII:

The same products as in the Test AI were tested in four greenhouses on in each case 200 vegetable plants which were strongly infested with white fly (*Aleyrodes proletella*) and various types of aphids (Aphididae).

The applied quantity in each case was 200 ml, i.e. 1 ml per plant, fully wetted.

Results:

With IAM 91 and with IAM 92 as well as with the application of REF (I) and REF (II) all plants were completely free of any infestation in the bonitures after 1, 4, 7 and 14 days.

6. Further Applications on Insects:

IAM 87 and IAM 88 were used comparatively in equal quantities to REF (I) and REF (II) in the laboratory experiment as spray agents for use against the following pests (adults and metamorphoses):
A) *Musca domestica*—Common House Fly
B) *Blatella germanica*—German Cockroach
C) *Lasius niger*—Black Garden Ant
D) *Ixodes ricinus*—Common Tick
E) *Tineola bisselliella*—Common Clothes Moth For the tests 30 samples each of the flying pests A) and E) were put into a cage covered with gauze with a size of 1×1×1 m and each was sprayed with 1 ml of the above quoted products. The animals incapable of flight and lying on the bottom were evaluated after respectively 1, 5, 10 and 20 minutes and also the mortality or revival rate (recuperation) after 24 hours.

Results in Percentage Mortality:

|  | Flies | | | | | Moths | | | | |
| --- | --- | --- | --- | --- | --- | --- | --- | --- | --- | --- |
|  | 1 | 5 | 10 | 20 min. | 24 hrs. | 1 | 5 | 10 | 20 min. | 24 hrs. |
| IAM 87 | 100 | 100 | 100 | 100 | 100 | 100 | 100 | 100 | 100 | 100 |
| IAM 88 | 100 | 100 | 100 | 100 | 100 | 100 | 100 | 100 | 100 | 100 |
| REF (I) | 20 | 80 | 100 | 100 | 95 | 100 | 100 | 100 | 100 | 100 |
| REF (II) | 10 | 70 | 100 | 100 | 100 | 90 | 100 | 100 | 100 | 100 |

For the creeping pests, similarly in each case 30 samples of mixed metamorphoses were placed in baths with dimensions 1×1×1 m and in each case sprayed with 1 ml—boniture as before.

|  | IAM 87 | | | | | REF(I) | | | | |
| --- | --- | --- | --- | --- | --- | --- | --- | --- | --- | --- |
|  | 1 | 5 | 10 | 20 min. | 24 hrs. | 1 | 5 | 10 | 20 min. | 24 hrs. |
| Cockroaches | 100 | 100 | 100 | 100 | 100 | 60 | 90 | 100 | 100 | 100 |
| Ants | 85 | 100 | 100 | 100 | 100 | 10 | 35 | 70 | 100 | 100 |
| Ticks | 40 | 60 | 100 | 100 | 100 | 0 | 0 | 20 | 40 | 100 |

|  | IAM 88 | | | | | REF (II) | | | | |
| --- | --- | --- | --- | --- | --- | --- | --- | --- | --- | --- |
|  | 1 | 5 | 10 | 20 min. | 24 hrs. | 1 | 5 | 10 | 20 min. | 24 hrs. |
| Cockroaches | 100 | 100 | 100 | 100 | 100 | 65 | 95 | 100 | 100 | 100 |
| Ants | 85 | 100 | 100 | 100 | 100 | 10 | 30 | 85 | 100 | 100 |
| Ticks | 55 | 100 | 100 | 100 | 100 | 0 | 25 | 60 | 100 | 100 |

The evaluation after the respective expired time acquired exclusively animals lying on their backs which showed no leg or antenna movement under the magnifying glass. Also these experimental setups showed that with the use of the insect repellent according to the invention surprisingly not only a comparable, expected effect could be achieved, but rather an effect could be achieved which was better than with the normal marketed comparative products REF (I) and REF (II).

The invention claimed is:

1. A method to repel an insect comprising applying to an object an insect repellent comprising an acyclic terpene ($C_{10}$), wherein said acyclic terpene is an acyclic terpene radical having two oxygen atom radicals with i) a terpene radical attached to one of said oxygen atom radicals and a hydrogen attached to the other oxygen atom radical or ii) a terpene radical attached to each of said oxygen atom radicals.

2. The method according to claim 1, wherein the terpene radical of i) or ii) is saturated.

3. The method according to claim 1, wherein the terpene radical of i) or ii) is single or double unsaturated.

4. The method according to claim 1, wherein the acyclic terpene radical exhibits one of the following structures:

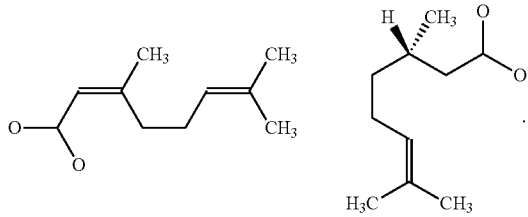

5. The method according to claim 4, wherein the acyclic terpene radical exhibits the following structure:

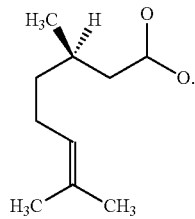

6. The method according to claim 1, wherein the acyclic terpene is a cis-3,7-dimethyl-2,6-octadienal-trans-3,7-dimethyl-2,6-octadienyl-acetal (neral geranylacetal, Structure 5a) or a cis-3,7-dimethyl-2,6-octadienal-di(trans-3,7-dimethyl-2,6-octadienyl)-acetal (neral digeranylacetal, Structure 5b).

7. The method according to claim 1, wherein the acyclic terpene is a cis-3,7-dimethyl-2,6-octadienal-R-(−)-3,7-dimethyl-1,6-octadien-3-yl-acetal (neral-(−)-linalylacetal, Structure 6a) or a cis-3,7-dimethyl-2,6-octadienal-di(R-(−)-3,7-dimethyl-1,6-octadien-3-yl)-acetal (neral di-(−)-linalylacetal, Structure 6b).

8. The method according to claim 1, wherein the acyclic terpene is a cis-3,7-dimethyl-2,6-octadienal-cis-3,7-dimethyl-2,6-octadienyl-acetal (neral nerylacetal, Structure 7a) or a cis-3,7-dimethyl-2,6-octadienal-di(cis-3,7-dimethyl-2,6-octadienyl)-acetal (neral dinerylacetal, Structure 7b).

9. The method according to claim 1, wherein the acyclic terpene is a trans-3,7-dimethyl-2,6-octadienal-trans-3,7-dimethyl-2,6-octadienyl-acetal (geranial geranylacetal, Structure 8a) or a trans-3,7-dimethyl-2,6-octadienal-di(trans-3,7-dimethyl-2,6-octadienyl)-acetal (geranial digeranylacetal, Structure 8b).

10. The method according to claim 1, wherein the acyclic terpene is a trans-3,7-dimethyl-2,6-octadienal-R-(+3,7-dimethyl-1,6-octadien-3-yl-acetal (geranial-(−)-linalylacetal, Structure 9a) or a trans-3,7-dimethyl-2,6-octadienal-di(R-(−)-3,7-dimethyl-1,6-octadien-3-yl)-acetal (geranial di-(−)-linalylacetal, Structure 9b).

11. The method according to claim 1, wherein the acyclic terpene is a trans-3,7-dimethyl-2,6-octadienal-cis-3,7-dimethyl-2,6-octadienyl-acetal (geranial nerylacetal, Structure 10a) or a trans-3,7-dimethyl-2,6-octadienal-di(cis-3,7-dimethyl-2,6-octadienyl)-acetal (geranial dinerylacetal, Structure 10b).

12. The method according to claim 1, wherein the acyclic terpene is an R-(+)-3,7-dimethyl-6-octenal-trans-3,7-dimethyl-2,6-octadienyl-acetal ((+)-citronellal geranylacetal, Structure 11a) or an R-(+)-3,7-dimethyl-6-octenal-di(trans-3,7-dimethyl-2,6-octadienyl)-acetal ((+)-citronellal digeranylacetal, Structure 11b).

13. The method according to claim 1, wherein the acyclic terpene is an R-(+)-3,7-dimethyl-6-octenal-R-(−)-3,7-dimethyl-1,6-octadien-3-yl-acetal ((+)-citronellal-(−)-linalylacetal, Structure 12a) or an R-(+)-3,7-dimethyl-6-octenal-di(R-(+3,7-dimethyl-1,6-octadien-3-yl)-acetal ((+)-citronellal di-(−)-linalylacetal, Structure 12b).

14. The method according to claim 1, wherein the acyclic terpene is an R-(+)-3,7-dimethyl-6-octenal-cis-3,7-dimethyl-2,6-octadienyl-acetal ((+)-citronellal nerylacetal, Structure 13a) or an R-(+)-3,7-dimethyl-6-octenal-di(cis-3,7-dimethyl-2,6-octadienyl)acetal ((+)-citronellal dinerylacetal, Structure 13b).

15. The method according to claim 1, wherein the acyclic terpene is an S-(−)-3,7-dimethyl-6-octenal-trans-3,7-dimethyl-2,6-octadienyl-acetal ((−)-citronellal geranylacetal, Structure 14a) or an S-(−)-3,7-dimethyl-6-octenal-di(trans-3,7-dimethyl-2,6-octadienyl)-acetal ((−)-citronellal digeranylacetal, Structure 14b).

16. The method according to claim 1, wherein the acyclic terpene is an S-(−)-3,7-dimethyl-6-octenal-R-(−)-3,7-dimethyl-1,6-octadien-3-yl-acetal ((−)-citronellal-(−)-linalylacetal, Structure 15a) or an S-(−)-3,7-dimethyl-6-octenal-di(R-(−)-3,7-dimethyl-1,6-octadien-3-yl)-acetal ((−)-citronellal di-(−)-linalylacetal, Structure 15b).

17. The method according to claim 1, wherein the acyclic terpene is an S-(−)-3,7-dimethyl-6-octenal-cis-3,7-dimethyl-2,6-octadienyl-acetal ((−)-citronellal nerylacetal, Structure 16a) or an S-(−)-3,7-dimethyl-6-octenal-di(cis-3,7-dimethyl-2,6-octadienyl)acetal ((−)-citronellal dinerylacetal, Structure 16b).

18. The method according to claim 1, wherein the acyclic terpene is an R-(+)-3,7-dimethyl-6-octenal-R-(+)-3,7-dimethyl-6-octenyl-acetal ((+)-citronellal-(+)-citronellylacetal, Structure 17a) or an R-(+)-3,7-dimethyl-6-octenal-di(R-(+)-3,7-dimethyl-6-octenyl)-acetal ((+)-citronellal di-(+)-citronellylacetal, Structure 17b).

19. The method according to claim 1, wherein the acyclic terpene is an R-(+)-3,7-dimethyl-6-octenal-S-(−)-3,7-dimethyl-6-octenyl-acetal ((+)-citronellal-(−)-citronellylacetal, Structure 18a) or an R-(+)-3,7-dimethyl-6-octenal-di(S-(+3,7-dimethyl-6-octenyl)-acetal ((+)-citronellal di-(−)-citronellylacetal, Structure 18b).

20. The method according to claim 1, wherein the acyclic terpene is an S-(−)-3,7-dimethyl-6-octenal-R-(+)-3,7-dimethyl-6-octenyl-acetal ((−)-citronellal-(+)-citronellylacetal, Structure 19a) or an S-(−)-3,7-dimethyl-6-octenal-di(R-(+)-3,7-dimethyl-6-octenyl)-acetal ((−)-citronellal di-(+)-citronellylacetal, Structure 19b).

21. The method according to claim 1, wherein the acyclic terpene is an S-(−)-3,7-dimethyl-6-octenal-S-(−)-3,7-dimethyl-6-octenyl-acetal ((−)-citronellal-(−)-citronellylacetal, Structure 20a) or an S-(−)-3,7-dimethyl-6-octenal-di(S-(−)-3,7-dimethyl-6-octenyl)-acetal ((−)-citronellal di-(−)-citronellylacetal, Structure 20b).

22. The method according to claim 1, wherein the acyclic terpene is a cis-3,7-dimethyl-2,6-octadienal-R-(+)-3,7-dimethyl-6-octenyl-acetal (neral-(+)-citronellylacetal, Structure 21a) or a cis-3,7-dimethyl-2,6-octadienal-di(R-(+)-3,7-dimethyl-6-octenyl)-acetal (neral di(+)-citronellyl acetal, Structure 21b).

23. The method according to claim 1, wherein the acyclic terpene is a trans-3,7-dimethyl-2,6-octadienal-R-(+)-3,7-dimethyl-6-octenyl-acetal (geranial-(+)-citronellylacetal, Structure 22a) or a trans-3,7-dimethyl-2,6-octadienal-di(R-(+)-3,7-dimethyl-6-octenyl)-acetal (geranial di(+)-citronellyl acetal, Structure 22b).

24. The method according to claim 1, wherein the acyclic terpene is a cis-3,7-dimethyl-2,6-octadienal-S-(−)-3,7-dimethyl-6-octenyl-acetal (neral-(−)-citronellylacetal, Structure 23a) or a cis-3,7-dimethyl-2,6-octadienal-di(S-(−)-3,7-dimethyl-6-octenyl)-acetal (neral di(−)-citronellyl acetal, Structure 23b).

25. The method according to claim 1, wherein the acyclic terpene is a trans-3,7-dimethyl-2,6-octadienal-S-(−)-3,7-dimethyl-6-octenyl-acetal (geranial-(−)-citronellylacetal, Structure 24a) or a trans-3,7-dimethyl-2,6-octadienal-di(S-(−)-3,7-dimethyl-6-octenyl)-acetal (geranial di(−)-citronellyl acetal, Structure 24b).

26. The method according to claim 1, wherein said insect repellent further comprises a saturated or unsaturated, aliphatic carboxylic acid C1-C12.

27. The method according to claim 1 wherein said insect repellent further comprises benzoate selected from trans-3,7-dimethyl-2,6-octadienyl benzoate (geranyl benzoate, Structure 45), cis-3,7-dimethyl-2,6-octadienyl benzoate (neryl benzoate, Structure 46), R-(−)-3,7-dimethyl-1,6-octadien-3-yl benzoate ((−)-linalyl benzoate, Structure 47), R-(+)-p-menth-1-en-8-yl benzoate ((+)-terpinyl benzoate, 48), S-(−)-p-menth-1-en-8-yl benzoate ((−)-terpinyl benzoate, 49), R-(+)-3,7-dimethyl-6-octenyl benzoate ((+)-citronellyl benzoate, R), S-(−) -3,7-dimethyl-6-octenyl benzoate ((−)-citronellyl benzoate, 51) or free benzoic acid or a mixture of these compounds.

28. The method according to claim 1, wherein said insect repellent further comprises p-mentha-3,8-diol, selected from cis-p-mentha-3,8-diol (cis-isopulegol hydrate, Structure 52) or trans-p-mentha-3,8-diol (trans-isopulegol hydrate, Structure 53) or a mixture of them.

29. The method according to claim 1, wherein said insect repellent further comprises hydroxy octanal selected from R-(+)-3,7-dimethyl-7-hydroxy octanal ((+)-citronellal hydrate, Structure 54) or an S-(−)-3,7-dimethyl-7-hydroxy octanal ((−)-citronellal hydrate, Structure 55) or a mixture of them.

30. The method according to claim 1, wherein said insect repellent further comprises (2=,4aR=,7R,8aR=,−2-((R)-2,6-dimethylhept-5-enyl)-4,4,7-trimethylhexohydro-benzo[1,3]dioxin (trans-(+)-citronellal-p-mentha-3,8-diylacetal, Structure 56) or (2=,4aR=,7R,8aS=,−2-((R)-2,6-dimethylhept-5-enyl)-4,4,7-trimethylhexohydro-benzo[1,3]dioxin (cis-(+)-citronellal-p-mentha-3,8-diylacetal, Structure 57) or (2=, 4aR=,7R,8aR=,−2-((S)-2,6-dimethylhept-5-enyl)-4,4,7-trimethylhexohydro-benzo[1,3]dioxin (trans-(−)-citronellal-p-mentha-3,8-diylacetal, Structure 58) or (2=,4aR=,7R, 8aS=,−2-(S)-2,6-dimethylhept-5-enyl)-4,4,7-trimethylhexohydro-benzo[1,3]dioxin (cis-(−)-citronellal-p-mentha-3,8-diylacetal, Structure 59) or containing a mixture of them.

31. The method of claim 1, wherein said insect repellent further comprises octanoic acid (caprylic acid) or decanoic acid (capric acid).

32. The method of claim 1, wherein said insect repellent further comprises a benzoate.

* * * * *